(12) United States Patent
Sirkar et al.

(10) Patent No.: US 9,452,930 B2
(45) Date of Patent: Sep. 27, 2016

(54) SYSTEM AND METHOD FOR CONTINUOUS POLYMER COATING OF PARTICLES

(71) Applicant: New Jersey Institute of Technology, Newark, NJ (US)

(72) Inventors: Kamalesh Sirkar, Bridgewater, NJ (US); Robert Pfeffer, Scottsdale, AZ (US); Dhananjay Singh, Kearny, NJ (US); Dengyue Chen, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 196 days.

(21) Appl. No.: 14/532,663

(22) Filed: Nov. 4, 2014

(65) Prior Publication Data

US 2015/0125590 A1 May 7, 2015

Related U.S. Application Data

(60) Provisional application No. 61/899,692, filed on Nov. 4, 2013.

(51) Int. Cl.
*A61K 9/50* (2006.01)
*B82Y 30/00* (2011.01)
*A61K 9/51* (2006.01)

(52) U.S. Cl.
CPC .............. *B82Y 30/00* (2013.01); *A61K 9/5192* (2013.01); *A61K 9/50* (2013.01)

(58) Field of Classification Search
CPC ........ B01J 13/02; A61K 9/50; A61K 9/5005
USPC ................. 427/212, 213.3, 213.34, 2.14
See application file for complete search history.

(56) References Cited

U.S. PATENT DOCUMENTS

| | | | | |
|---|---|---|---|---|
| 6,482,438 B1* | 11/2002 | Singh | .................. | A61K 9/1688 424/450 |
| 7,709,054 B2* | 5/2010 | Mao | ......................... | C30B 7/00 427/177 |
| 2002/0160109 A1* | 10/2002 | Yeo | ...................... | A61K 9/5031 427/213.3 |
| 2003/0146529 A1* | 8/2003 | Chen | ........................ | B01J 13/06 264/4.1 |
| 2005/0191491 A1* | 9/2005 | Wang | .................... | A61K 9/5089 428/407 |
| 2006/0096525 A1* | 5/2006 | Sirkar | ....................... | C30B 7/00 117/200 |
| 2006/0182808 A1* | 8/2006 | Bakker | ................. | A61K 9/1688 424/489 |
| 2007/0107884 A1* | 5/2007 | Sirkar | .................. | F28D 7/1669 165/133 |
| 2011/0014110 A1* | 1/2011 | Sirkar | ...................... | C30B 7/00 423/397 |
| 2011/0306539 A1* | 12/2011 | Shen | ........................ | A61K 9/14 514/1.1 |

* cited by examiner

*Primary Examiner* — Cachet Sellman
(74) *Attorney, Agent, or Firm* — McCarter & English, LLP

(57) ABSTRACT

The present disclosure relates to the field of polymer coating. The present disclosure provides improved systems and methods for continuous polymer coating of particles (e.g., nanoparticles). The present disclosure provides for a solid hollow fiber cooling crystallization (SHFCC) technique to continuously coat the nanoparticles with polymer. In certain embodiments, the present disclosure embraces continuous coating of particles from about 1 nm to about 10 microns. A polymer solution containing a suspension of submicron particles flows in the lumen of a solid polymeric hollow fiber, and controlled cooling of the polymer solution allows for polymer nucleation on the surface of the particles, and the precipitated polymer forms a thin film around the particles (the thickness of which can be varied depending on the operating conditions). The systems, methods and assemblies of the present disclosure are easily adaptable for coating nano-sized drug particles as well.

20 Claims, 20 Drawing Sheets

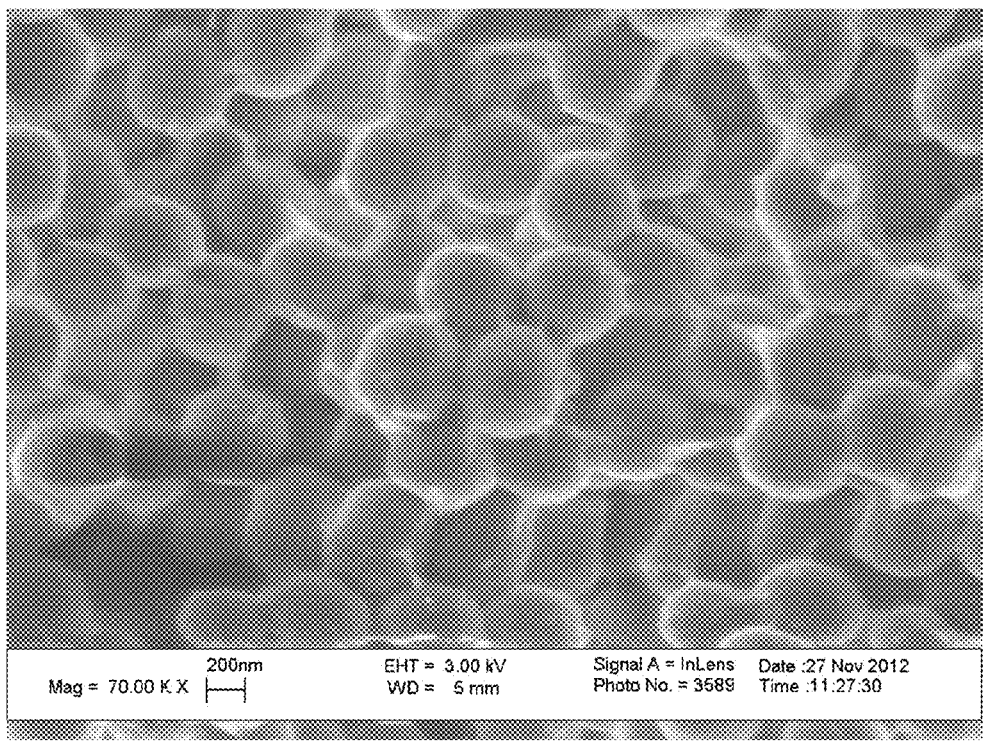
FIGURE 13A1
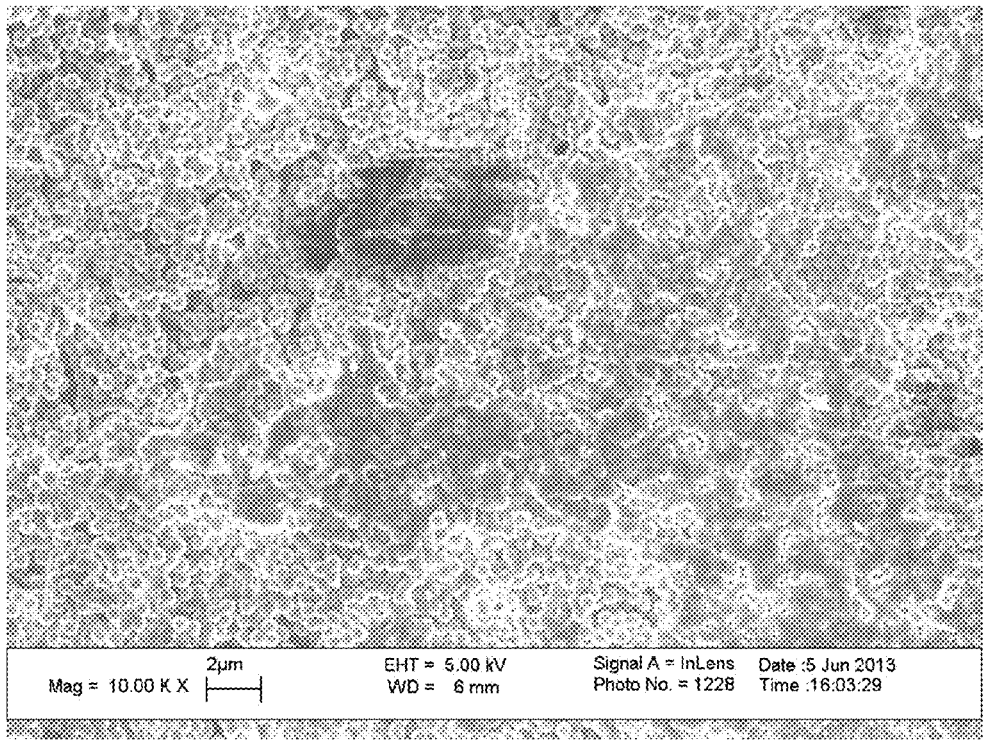
FIGURE 13A2

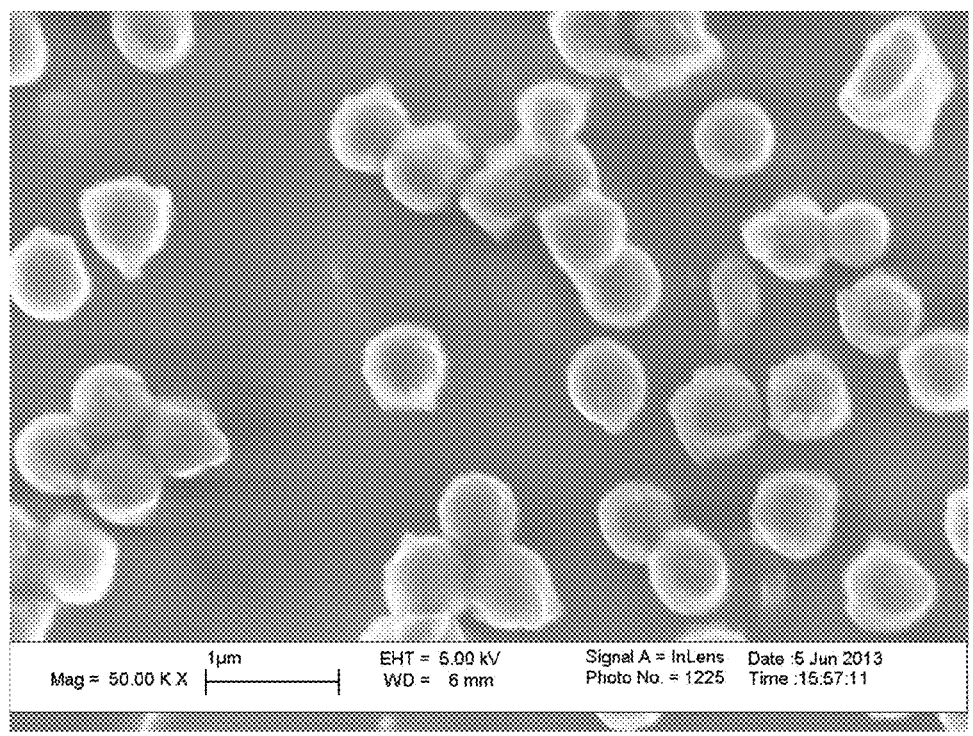
FIGURE 13B1
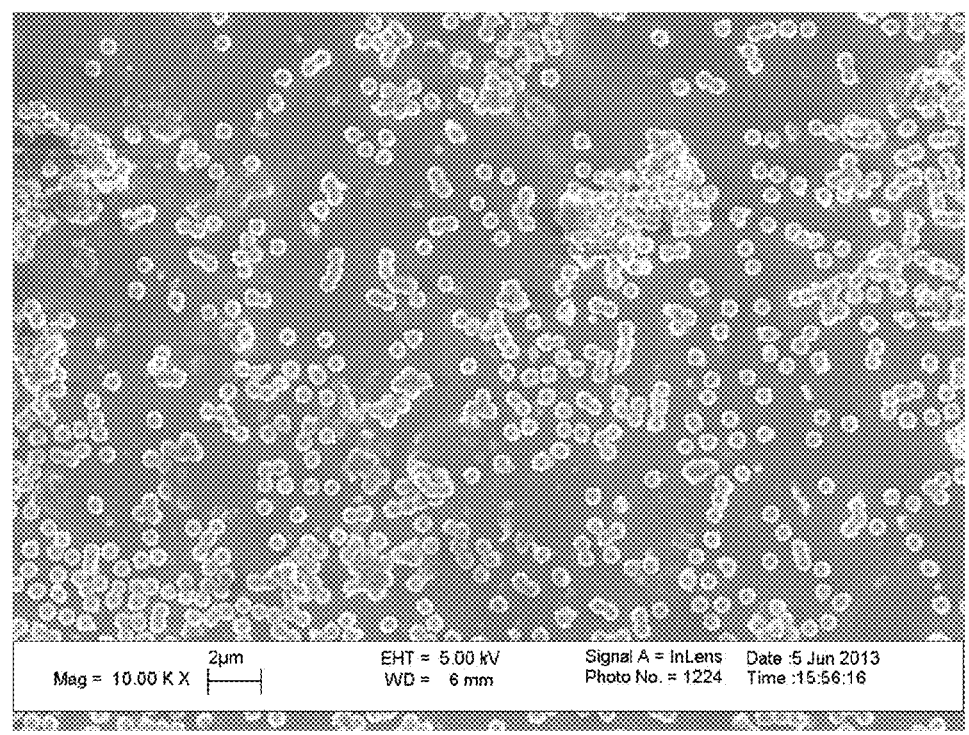
FIGURE 13B2

SYSTEM AND METHOD FOR CONTINUOUS POLYMER COATING OF PARTICLES

CROSS-REFERENCE TO RELATED APPLICATIONS

This application claims the benefit of U.S. Provisional Application Ser. No. 61/899,692 filed Nov. 4, 2013, the contents of which are herein incorporated by reference in their entirety.

STATEMENT REGARDING FEDERALLY SPONSORED RESEARCH

This invention was made with government support under Grant CMMI-1100622 through the National Science Foundation. The government has certain rights in the invention.

FIELD OF THE DISCLOSURE

The present disclosure relates to the field of polymer coating and, more particularly, to improved systems and methods for continuous polymer coating of particles (e.g., nanoparticles).

BACKGROUND OF THE DISCLOSURE

In general, nanoparticle-based drug delivery systems are of interest in, inter alia, controlled release of drugs, delivery of anticancer drugs and imaging agents to tumors, tuberculosis treatment and as non-viral gene delivery vehicles. Some important advantages of nanoparticles in drug delivery systems are greater solubility, high stability, high carrier capacity, incorporation of biodegradable hydrophilic/hydrophobic substances and different ways of administering the drug including oral, injection, and inhalation methods. These desirable properties can improve drug bioavailability and patient compliance by reduced drug administration frequency.

In some drug delivery systems, each drug has a concentration range providing optimal therapeutic effects. When the concentration falls out of this range (either higher or lower), it may cause toxic effects or become therapeutically ineffective. Therefore, it can be desirable to release the drug from a polymer carrier in a sustained or a controlled manner. In general, a polymer carrier can also provide protection for fragile drugs (e.g., proteins and peptides) from hydrolysis and degradation. Protection from stomach acids is a good example since even small drug molecules such as erythromycin can be irritating to the gastric mucosa.

Lai et al. ("*Mucus-penetrating nanoparticles for drug and gene delivery to mucosal tissues,*" Adv. Drug Deliv. Rev., 61 (2):158-171 (2008)) recently demonstrated that nanoparticles, if sufficiently coated with a muco-inert polymer such as lower molecular weight PEG, can rapidly traverse physiological human mucus with diffusivities almost as high as those in pure water. This finding suggests that it is possible to engineer (e.g., coat) nano-sized drug particles to overcome the mucus barrier, allowing sustained drug delivery to specific cells in the body at mucosal surfaces and provide improved efficacy and reduced side effects for a wide range of therapeutics.

In general, the potential for nanoparticles to revolutionize drug delivery systems is large. However, a number of problems need to be overcome including, for example, continuously layering and coating nanoparticles with polymeric materials to achieve time release, protecting them from stomach acids and being trapped by a mucus barrier, or preventing immune cells (macrophages) from engulfing and eliminating the nanoparticles circulating in the bloodstream. Nanoparticle surface coating or tailoring can also provide a variety of desirable properties in physical, optical, electronic, and chemical applications.

Conventional methods for coating or encapsulating micron-sized and nanoparticles utilize dry or wet approaches. For example, Wang et al. ("*Polymer Coating/encapsulation of Nanoparticles using a Supercritical Antisolvent Process,*" J. Supercritical Fluids, 28, 84 (2004)) has summarized some of these approaches: dry methods include physical vapor deposition, plasma treatment, chemical vapor deposition, and pyrolysis of polymeric organic materials; wet methods cover sol-gel processes, emulsification and solvent evaporation techniques. Supercritical fluid processes such as rapid expansion of supercritical solutions (RESS), supercritical anti-solvent (SAS), and gas anti-solvent (GAS) processes employing supercritical $CO_2$ are alternative methods for nanoparticle coating or encapsulation of ultrafine particles. For example, Yue et al. ("*Particle Encapsulation with Polymers via in-situ Polymerization in Supercritical $CO_2$*", Powder Technology, 146 (1-2), 32 (2004)) encapsulated hydrocortisone with polyvinylpyrrolidone (PVP) by in situ dispersion polymerization in supercritical $CO_2$.

These processes have many shortcomings. Some processes, e.g., supercritical $CO_2$-based processes ("*$SmCO_5$/CU Particles Elaboration using a Supercritical Fluid Process*", J. Alloys Compounds, 323, 412 (2001)), require demanding operating conditions (pressure about 190 MPa); SAS processes require significantly lower pressure about 10 MPa which is still high. RESS processes (e.g., Kim et al., "*Microencapsulation of Naproxen using Rapid Expansion of Supercritical Solutions*", Biotechnol. Prog. 12, 650 (1996)) encounter low polymer solubility in supercritical $CO_2$ at lower temperatures (less than 80° C.) and can use very few polymers which may lack bio-degradability or time release due to their limited $CO_2$ solubility. Most of these techniques are also batch processes.

Fluidized bed-based processes (e.g., Tsutsumi et al. "*A Novel Fluidized-bed Coating of Fine Particles by Rapid Expansion of Supercritical Fluid Solutions*", Powder Technol., 85, 275 (1995)), which can be continuous, face problems due to nanoparticle fluidization difficulties caused by van der Waals and other interparticle forces. In such processes, scale-up is also quite demanding. Nanoparticles, which tend to agglomerate rapidly in the dry state because of their large interparticle forces due to their small size, will typically only accentuate these problems when they are coated with polymers via precipitation/crystallization, etc.

Scale-up problems in conventional batch crystallizers which are usually stirred vessels include the problems of imperfect mixing and non-uniform conditions leading to a broad crystal size distribution (CSD). New monitoring techniques (e.g., Gron et al., "*In-Process ATR-FTIR Spectroscopy for Closed-loop Supersaturation Control of a Batch Crystallizer Producing Monosodium Glutamate Crystals of Defined Size,*" Ind. Eng. Chem. Res., 42, 198 (2003)) can lead to better prediction and control of the applied supersaturation in crystallizers. However, well-mixed crystallizers are intrinsically inclined toward a spectrum of local conditions in time and space and consequently a relatively broad CSD. To overcome these problems, a novel crystallizer design based on a hollow fiber device has been proposed (Zarkadas et al., "*Solid Hollow Fiber Cooling Crystallization*", Ind. Eng. Chem. Res., 43, 7163 (2004)).

Thus, an interest exists for improved systems and methods for continuous polymer coating of particles (e.g., nanoparticles). These and other inefficiencies and opportunities for improvement are addressed and/or overcome by the assemblies, systems and methods of the present disclosure.

SUMMARY OF THE DISCLOSURE

The present disclosure provides advantageous systems and methods for continuous polymer coating of particles (e.g., nanoparticles).

In general, there is no current technique available to continuously film coat nano-sized drug particles with a polymer to produce large amounts of free-flowing coated particles. In exemplary embodiments and after determining the cloud point of the polymer solutions by UV spectrophotometry, the present disclosure provides for a solid hollow fiber cooling crystallization (SHFCC) technique to continuously coat the nanoparticles with polymer. In certain embodiments, the present disclosure embraces continuous coating of particles from about 1 nm to about 10 microns.

In some embodiments, a polymer solution containing a suspension of submicron particles flows in the lumen of a solid polymeric hollow fiber. Controlled cooling of the polymer solution allows for polymer nucleation on the surface of the particles, and the precipitated polymer forms a thin film around the particles, the thickness of which can be varied depending on the operating conditions. Scanning electron microscopy (SEM), transmission electron microscopy (TEM), energy dispersive X-ray spectrometry (EDS), laser diffraction spectroscopy (LDS) and thermogravimetric analysis (TGA) have been utilized to characterize the coatings. The results indicate that a uniformly coated and free-flowing product can been achieved under optimized conditions in the SHFCC (and suitable post-treatments). Furthermore, scale-up of the method can be easily accomplished by using a larger SHFCC module containing a much larger number of solid hollow fibers. The systems, methods and assemblies of the present disclosure are easily adaptable for coating nano-sized drug particles as well.

The present disclosure provides for a method for coating particles including: a) providing a polymer solution containing a suspension of particles; b) flowing the polymer solution through a lumen of a hollow fiber; and c) passing a cooling fluid around the exterior of the hollow fiber to cool the polymer solution and allow for polymer nucleation on the particles, with precipitated polymer forming a film around the particles to form uniformly coated and free-flowing coated particles.

The present disclosure also provides for a method for coating particles wherein the particles in the polymer solution have a particle size of about 1 nm to about 10 microns. The present disclosure also provides for a method for coating particles wherein the hollow fiber is a polymeric hollow fiber, the polymeric hollow fiber having a solid non-porous and non-permeable wall that defines the lumen.

The present disclosure also provides for a method for coating particles wherein the polymer solution includes a copolymer of ethyl acrylate, methyl methacrylate and a content of methacrylic acid ester. The present disclosure also provides for a method for coating particles wherein the polymer solution includes Poly(D,L-lactide-co-glycolide).

The present disclosure also provides for a method for coating particles wherein the hollow fiber is fabricated from polypropylene. The present disclosure also provides for a method for coating particles wherein the hollow fiber has an internal diameter of about 420 µm and an outer diameter of about 575 µm.

The present disclosure also provides for a method for coating particles wherein the polymer solution includes acetone, water and a surfactant. The present disclosure also provides for a method for coating particles wherein the polymer solution is pumped through the lumen of the hollow fiber at a rate of about 2.5 ml/minute.

The present disclosure also provides for a method for coating particles wherein the cooling fluid includes ethylene glycol. The present disclosure also provides for a method for coating particles wherein the cooling fluid is configured to cool the polymer solution from about 55° C. to about 5° C. to form the coated particles.

The present disclosure also provides for a method for coating particles further including the step of: d) filtering the solution containing the coated particles that exits the hollow fiber. The present disclosure also provides for a method for coating particles further including the step of: e) adding water under sonication to the filtered coated particles.

The present disclosure also provides for a method for coating particles wherein step d) includes utilizing a vacuum filtration device.

The present disclosure also provides for a method for coating particles further including the step of: d) centrifuging the solution containing the coated particles that exits the hollow fiber.

The present disclosure also provides for a method for coating particles further including the step of: e) adding water under sonication to the centrifuged coated particles.

The present disclosure also provides for a method for coating particles wherein the polymer solution includes sodium dodecyl sulfate. The present disclosure also provides for a method for coating particles wherein the coating thickness of the polymer film on the coated particles is about 20 nm.

The present disclosure also provides for a method for coating particles including: a) providing a polymer solution containing a suspension of particles, the particles in the polymer solution having a particle size of about 1 nm to about 10 microns; b) flowing the polymer solution through lumens of a plurality of polymeric hollow fibers; and c) passing a cooling fluid around the exterior of the plurality of the polymeric hollow fibers to cool the polymer solution and allow for polymer nucleation on the particles, with precipitated polymer forming a film around the particles to form uniformly coated and free-flowing coated particles.

The present disclosure also provides for a method for coating particles including: a) providing a polymer solution containing a suspension of drug particles, the drug particles in the polymer solution having a particle size of about 1 nm to about 10 microns; b) pumping the polymer solution through lumens of a plurality of polymeric hollow fibers, each polymeric hollow fiber having a solid non-porous and non-permeable wall that defines its respective lumen; c) passing a cooling fluid around the exterior of the plurality of the polymeric hollow fibers to cool the polymer solution and allow for polymer nucleation on the drug particles, with precipitated polymer forming a film around the drug particles to form uniformly coated and free-flowing coated drug particles; d) filtering the solution containing the coated drug particles that exits the hollow fibers; and e) adding water under sonication to the filtered coated drug particles.

Any combination or permutation of embodiments is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Exemplary embodiments of the present disclosure are further described with reference to the appended figures. It is to be noted that the various steps, features and combinations of steps/features described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein:

(FIG. 10A) 1 ml/min; (FIG. 10B) 5 ml/min, and (FIG. 10C) 10 ml/min;

(FIG. 11A) slow—1 in Hg; (FIG. 11B) fast—16 in Hg;

FIG. 12A-3 drops; FIG. 12B-5 drops, and FIG. 12C-15 drops;

FIGS. 13A1-B2 are SEM photographs of Eudragit RL 100 coated particles without post treatment after filtration (FIGS. 13A1 and 13A2) and with post treatment after filtration (FIGS. 13B1 and 13B2);

DETAILED DESCRIPTION OF DISCLOSURE

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, the technical and scientific terms used herein have the same meaning as commonly understood by one of ordinary skill in the art. The terminology used in the description of the disclosure herein is for describing particular embodiments, and is not intended to be limiting of the disclosure. All publications, patent applications, patents, figures and other references mentioned herein are expressly incorporated by reference in their entireties.

The exemplary embodiments disclosed herein are illustrative of advantageous systems and methods for continuous polymer coating of particles (e.g., nanoparticles). It should be understood, however, that the disclosed embodiments are merely exemplary of the present disclosure, which may be embodied in various forms. Therefore, details disclosed herein with reference to exemplary systems/assemblies and associated processes/techniques of assembly and use are not to be interpreted as limiting, but merely as the basis for teaching one skilled in the art how to make and use the advantageous systems, assemblies and methods of the present disclosure.

The present disclosure provides improved systems and methods for continuous polymer coating of particles (e.g., nanoparticles, drug particles, etc.).

In exemplary embodiments, the present disclosure provides for a solid hollow fiber cooling crystallization (SHFCC) technique to continuously coat the particles (nanoparticles) with polymer. In some embodiments, the present disclosure embraces continuous coating of particles from about 1 nm to about 10 microns. A polymer solution containing a suspension of submicron particles flows in the lumen of a solid polymeric hollow fiber, and controlled cooling of the polymer solution allows for polymer nucleation on the surface of the particles, and the precipitated polymer forms a thin film around the particles (the thickness of which can be varied depending on the operating conditions). The systems, methods and assemblies of the present disclosure are easily adaptable for coating nano-sized drug particles as well.

Current practice provides that there generally is no current technique available to continuously film coat nano-sized drug particles with a polymer to produce large amounts of free-flowing coated particles. In exemplary embodiments, the present disclosure provides for a solid hollow fiber cooling crystallization (SHFCC) technique to continuously coat the particles (e.g., nanoparticles) with polymer, thereby providing a significant manufacturing, commercial and/or operational advantage as a result.

Figure 1:
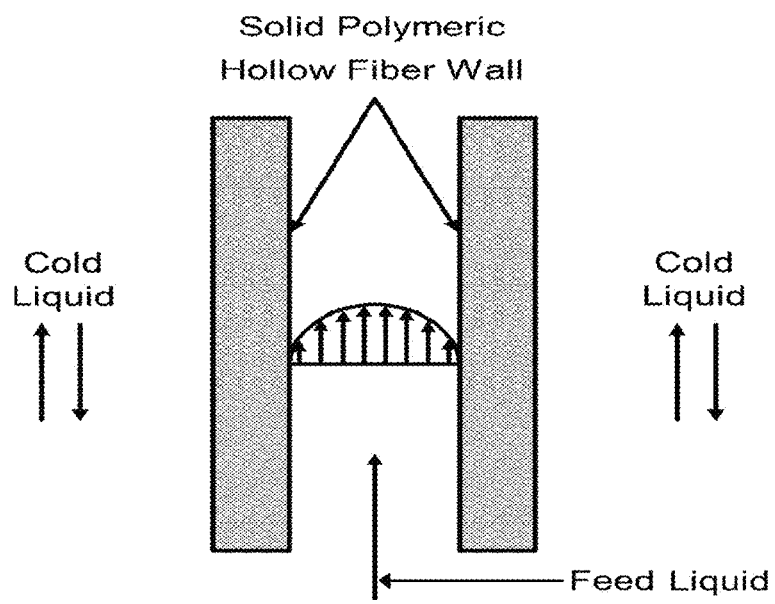
FIG. 1 depicts an exemplary solid hollow fiber cooling crystallizer (SHFCC)

FIG. 1 shows a single polymeric hollow fiber whose wall is solid (e.g., non-porous and/or non-permeable/impervious). The internal diameter (I.D.) of this particular fiber is about 420 μm, and the outer diameter (O.D.) is about 575 μm. This exemplary polymeric hollow fiber is fabricated from polypropylene (PP), which has a great deal of chemical, pH, and solvent resistance. It is noted that one could also employ a variety of other polymers, polytetrafluoroethylene (PTFE), polyimide, etc., for the hollow fiber. Polymers PP and PTFE in hollow fiber form are particularly useful since their smooth and non-sticky surfaces do not easily allow accumulation of precipitating crystals as long as the liquid is flowing.

In other embodiments, it is noted that the hollow fiber may include a wall that is porous (e.g., as long as the pores are not wetted by the polymer solution/suspension and the cooling liquid outside). Further, in certain embodiments, the cooling liquid/fluid outside (the fibers) should be non-volatile and should not add by its vapor anything deleterious to the polymer solution/suspension of drug particles.

In certain embodiments, the solution slated for crystallization was allowed to pass through the bore (or lumen) of the solid hollow fiber, and a coolant/fluid flow was provided on the outside of this fiber, thereby setting up heat exchange. In certain embodiments, fibers were made a part of a cylindrical heat exchange device packed with many such solid wall hollow fibers (FIG. 2), to essentially bundle together many long microfluidic channels in one small device. However, here the channels are substantially circular and the channel dimensions are considerably (almost by an order of magnitude) larger than conventional microfluidic channels.

Researchers (e.g., Zarkadas et al., "*Polymeric Hollow Fiber Heat Exchangers: an Alternative for Lower Temperature Applications,*" Ind. Eng. Chem. Res., 43, 8093 (2004)) have experimentally demonstrated that such a 30 cm long polymeric hollow fiber heat exchanger (PHFHE) is highly efficient compared to other heat exchangers due to the very large heat exchange surface area/volume (1400 m$^{-1}$) created by the polymeric hollow fiber surface area. Larger heat exchangers have been successfully tested in systems with precipitating salts of $CaSO_4$, $CaCO_3$ (e.g., Lee et al., "*Desalination with a Cascade of Crossflow Hollow Fiber Membrane Distillation Devices Integrated with a Hollow Fiber Heat Exchanger,*" AIChE J., DOI: 10:1002/aic.12409).

For cooling crystallization from a solution flowing through the hollow fiber bore with the coolant/fluid flowing on the shell side, the SHFCC was highly efficient for both aqueous and organic crystallizing solutions (Zarkadas et al., "*Solid Hollow Fiber Cooling Crystallization,*" Ind. Eng. Chem. Res., 43, 7163 (2004)). Examples illustrated include: crystallizing $KNO_3$ from an aqueous solution, salicyclic acid from ethanol, and paracetamol from an aqueous solution (e.g., Zarkadas et al., "*Cooling Crystallization of Paracetamol in Hollow Fiber Devices,*" Ind. Eng. Chem. Res., 46, 2928 (2007)).

The number of crystals generated/unit volume was 2-3 orders of magnitude higher, CSDs were much narrower, and the mean crystal sizes were 3-4 times smaller than those from conventional mixed suspension mixed product removal (MSMPR) crystallizers. The very low temperature difference between the SHFCC fiber wall and the crystallizing solution (about 1-2° C.) provided a far greater control over nucleation/crystal growth process.

In a PHFHE performing as a SHFCC, and in certain embodiments of the present disclosure, each hollow fiber acts as a separate crystallizer. As such, it is as if the feed solution has been sub-divided into numerous identical fluid packets traveling through each hollow fiber bore with the same velocity and under the same cooling conditions created by the flowing shell side cooling fluid. Therefore, the scale-up problem is minimized which is a major strength of SHFCC devices (e.g., Zarkadas et al., "*Polymeric Hollow Fiber Heat Exchangers: an Alternative for Lower Temperature Applications,*" Ind. Eng. Chem. Res., 43, 8093 (2004)). It is noted that if a few hollow fibers get accidentally blocked, the disturbance to the rest of the fiber assembly is minimal since in a 2.54 cm diameter module, there may be as many as 90 hollow fibers; in a 5.08 cm diameter module, there will be about 360 fibers. It is noted that that the fiber bore side flow Reynolds number is quite low (less than 500) to achieve the type of heat exchange as well as crystallization performances observed.

Therefore the pressure drops in the PHFHEs are much lower, as low as 1 kPa/NTU (NTU is the number of transfer units) compared to 30 kPa/NTU for conventional metallic heat exchangers. For the same pumping cost, PHFHEs transfer 5-20 times more heat per unit volume than typical shell-and-tube heat exchangers; this translates immediately into a much more efficient cooling crystallizer. The systems and methods of the present disclosure advantageously utilized similar PHFHE devices for continuous nanoparticle coating.

The hollow fiber I.D. in SHFCC devices studied was about 420 µm; therefore a clogging problem with nanoparticles or submicron particles is unlikely in the SHFCC devices. If a high level of nanoparticle agglomeration yields particle sizes about 1-2 µm; hollow fiber devices routinely handle such particles. The dissolved polymer in the solution can precipitate onto nanoparticles present if the temperature is reduced appropriately in the SHFCC device. If nanoparticles are present in a significant volume fraction, it is unlikely that polymer precipitation will create a network spanning the cross section of the tube I.D. Residence time control however has to be balanced against excessive coating of the particles.

The present disclosure utilizes a novel heat exchanger/crystallizer to continuously produce coated drug nanoparticles to achieve controlled drug release in a simple and controllable way that is suitable for scale up. The exemplary model submicron particles used to prove the concept were Cosmo 55 non-porous hydrophilic silica nanoparticles of 550 nm size; however, much smaller silica nanoparticles and actual drug nanoparticles supplied could also be used. In certain embodiments, the present disclosure embraces coating particles from a size of about 1 nm to about 10 microns. In some embodiments, coating polymers employed are Eudragit RL 100 and PLGA (Poly(D,L-lactide-co-glycolide)); both are biocompatible co-polymers which are widely used as an encapsulation agent in the pharmaceutical industry. It is noted that a wide array of other like polymers would also be acceptable and are embraced by the present disclosure.

Coating polymers used for certain exemplary embodiments were Eudragit RL 100 (a copolymer of ethyl acrylate, methyl methacrylate and a low content of methacrylic acid ester), $M_w$, 150,000, (Evonik-Degussa, Parsippany, N.J.); and PLGA (Poly(D,L-lactide-co-glycolide), $M_w$, 7,000-17,000), (Sigma-Aldrich, St. Louis, Mo.). Surrogate host particles were Cosmo 50 non-porous hydrophilic silica nanoparticles, 550 nm, (Presperse, Somerset, N.J.). Acetone, a good solvent for Eudragit RL 100, and dioxane, a good solvent for PLGA, were obtained from Aldrich. Sodium dodecyl sulfate, used as a surfactant, was purchased from Aldrich. The materials were used as received.

Figure 2:
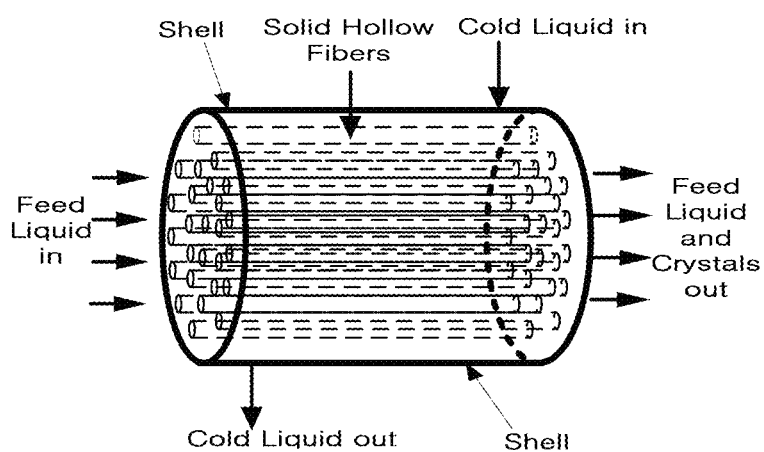
FIG. 2 depicts a schematic of a solid hollow fiber crystallizer/heat exchanger.

FIG. 2 shows solid hollow fibers inside the shell-and-tube SHFCC. The polymeric hollow fiber of polypropylene can resist chemicals such as dioxane and acetone; the surface of the nonporous and/or non-permeable/impervious wall of the fiber is smooth and non-sticky so that the precipitating polymers/crystals will not stick to the wall as long as the solution is flowing. The crystallization solution passed through the lumen side of the hollow fiber; the cooling liquid passed through the shell side extracting heat through the wall so that polymer in the solution precipitates onto the surrogate silica particles present in the solution flowing through the fiber bore. Eventually, the coated particles flow out of the SHFCC along with the solution.

Two sizes of SHFCC modules were constructed (see Table 1) in order to compare the module size effect and number of fibers on coating capacity, thickness, and scale-up. However, modules of any size could be made. The shell of both exemplary modules was made of FEP-based polymer tubing containing 23 or 46 solid PP hollow fibers. In certain embodiments, both ends are potted with an epoxy resin to form a tube sheet.

TABLE 1

Specifications of solid hollow fiber cooling crystallizer (SHFCC) modules.

| | Internal diameter | Outer diameter | Material | Number of fibers | Length | Shell diameter |
|---|---|---|---|---|---|---|
| Small module | 420 μm | 575 μm | Polypropylene (PP) | 23 | 47 cm | 8 mm |
| Large module | 420 μm | 575 μm | Polypropylene (PP) | 46 | 47 cm | 14 mm |

Figure 3A:
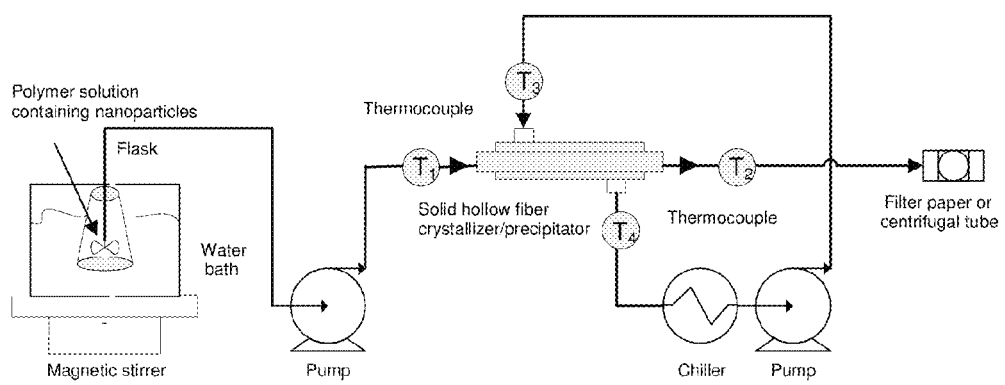
FIG. 3A shows a schematic diagram of an exemplary solid hollow fiber crystallization setup for continuous polymer coating of particles (e.g., coating of submicron particles and/or nanoparticles)

A schematic diagram of a coating setup of one embodiment of the present disclosure is shown in FIG. 3A. In one embodiment, a certain amount of polymer is introduced into a vessel containing acetone under stirring. After the polymer fully dissolved in acetone, a given amount of DI water is added. Then host silica particles and surfactant were added into the flask.

After about 30 minutes of stirring, the flask containing the well-mixed solution was put in a water bath at a constant temperature (55° C.). The solution was then fed into the lumen side of the SHFCC by a pump (Masterflex, model no. 7523-20, Cole-Parmer, Vernon Hills, Ill.) at a rate of 3.5 ml/min. The temperature indicated by thermocouple T1 was 55° C., the inlet temperature of the solution.

At the same time, an aqueous cooling solution of 50% by volume of ethylene glycol was circulated through the shell side to cool down the solution in the lumen side from about 55° C. to about 5° C. (unless otherwise mentioned) to initiate crystallization in the lumen side of the hollow fibers. A chiller (Polystat CR250WS, Cole-Parmer, Vernon Hills, Ill.) cooled the glycol solution to −9° C. in the shell side.

The solution containing coated particles at an outlet temperature (T2) of 5° C. was passed through a microfiltration system (Omnipore Membrane 02500, PTFE, hydrophobic, 0.45 μm pore size, 25 mm filter diameter, Millipore, Billerica, Mass.) to remove most of the solution; the cake on the filter paper containing the coated nanoparticles was collected for post-treatment and characterization.

In exemplary embodiments, two methods were used to collect samples of coated particles from the polymer solution leaving the cooling crystallizer/precipitator. Other embodiments of the present disclosure embrace other suitable methods.

Method 1 (centrifugation) involved collecting the solution from the outlet of the crystallizer-precipitator in a centrifuge tube. After 1 minute of centrifugation, the supernatant liquid was decanted leaving the product particles coated by polymer. The particles were subjected to vacuum drying and used for further characterization.

The second method employed filtration. After the coated particles and solution came out of the SHFCC outlet, a vacuum filtration device was employed to collect the sample. After filtration, the coated particles were collected on a filter paper and subjected to vacuum drying and used for further characterization.

In certain embodiments, to get free-flowing particles, an additional post treatment method was developed for both filtration and centrifugation. After filtration, particles remained on the filter paper and formed a cake. The cake on the filter paper was then placed into DI water under sonication for about 30 seconds to break-up loose agglomerates. The solution containing the dispersed particles was then decanted onto an aluminum dish and subjected to vacuum drying. Results showed that the dry particles were much more free-flowing than before sonication.

Figure 3B:
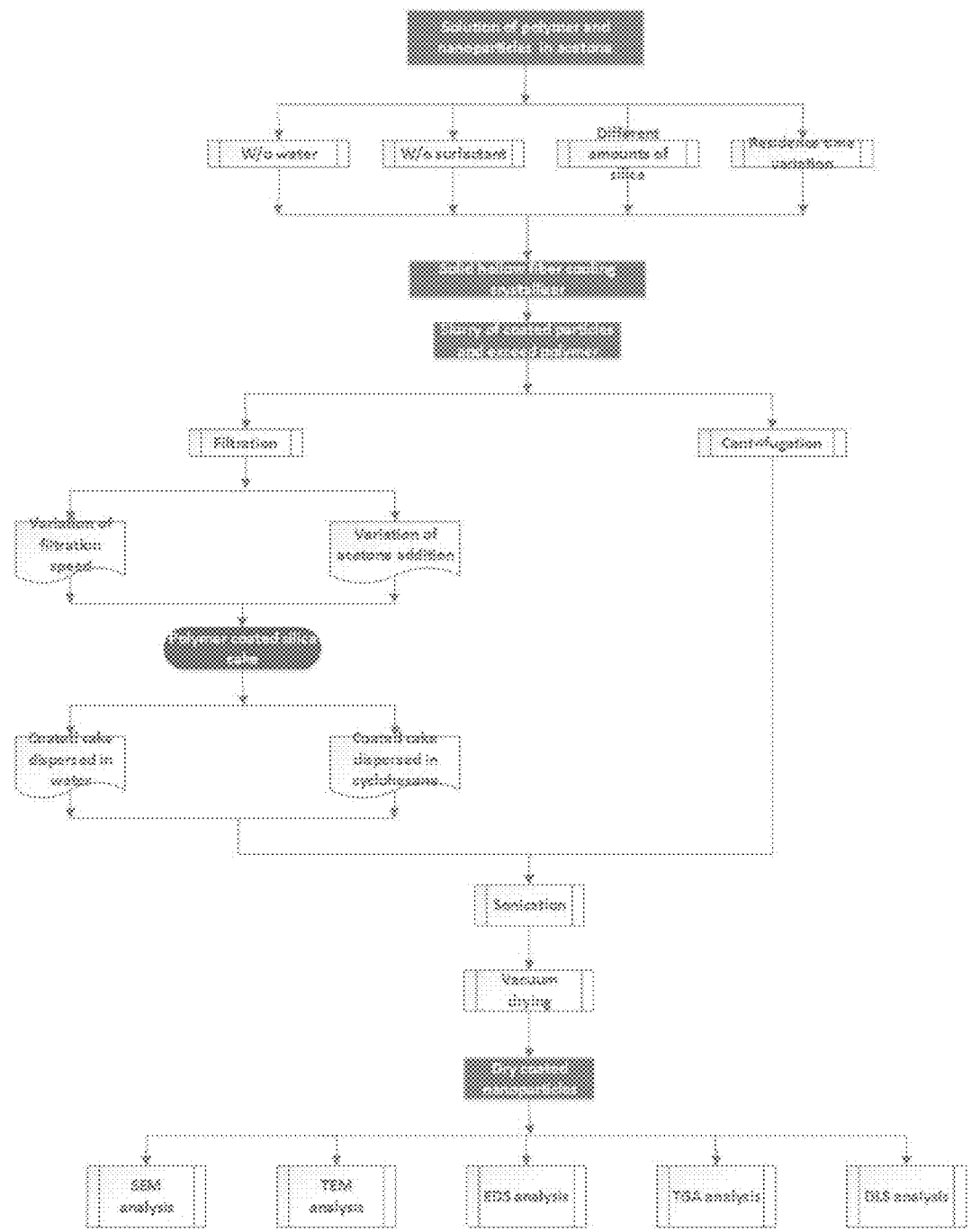
FIG. 3B shows exemplary procedures to obtain and characterize particles coated in the SHFCC device.

Post treatment sonication was also performed after centrifugation in certain embodiments. After the supernatant liquid was decanted, instead of collecting particles from the residue inside the centrifuge tube, some water was added to the tube and the tube was subjected to sonication for about 30 seconds to break-up the agglomerates. The supernatant liquid was poured out and the centrifugation process was repeated once more to remove any excess solution. The particles were then decanted into an aluminum dish and subjected to vacuum drying. An exemplary overview of the detailed procedures to obtain the coated particles in the SHFCC device, post-treat them and characterize the nature of the coating and the particle size distribution is provided in FIG. 3B.

It was desired to measure the cloud point of the Eudragit RL 100 or PLGA polymer solutions. There are two main ways of determining the cloud points of polymeric solutions, either by a UV spectrophotometer or by a refractometer. A Cary 50 UV spectrophotometer (Agilent, Santa Clara, Calif.) having a temperature controller module was used in the present disclosure. By identifying the absorbance or transmissivity of the solution in the visible wavelength range (550-800 nm), the cloud point could be easily determined.

The exemplary procedure followed (steps 1-5 below) for determining the cloud point of the binary system of polymer in organic solvent is as follows:

1. From the specification document of Cole-Parmer (e.g., http://eudragitevonik.com/product/eudragit/Documents/evonik-specifications-eudragit-rl-100,rl-po,rs-100,rs-po.pdf), the concentration of Eudragit in the solution at the cloud point temperature of 25° C. should be around 0.2 g/ml. To locate the cloud point concentration accurately, twelve samples of this polymer solution were prepared (the concentrations were 0, 0.14 g/ml, 0.16 g/ml, 0.18 g/ml, 0.20 g/ml, 0.24 g/ml, 0.26 g/ml, 0.28 g/ml, 0.30 g/ml, 0.32 g/ml, 0.34 g/ml and 0.36 g/ml).

2. A baseline correction was run in the UV spectrophotometer in which pure acetone was chosen as baseline to reduce the impact of acetone; after scanning the peak, the characteristic peak of Eudragit RL 100 was found at a wavelength of 335 nm.

3. A concentration program was then run to obtain a concentration vs. absorbance plot.

4. A concentration of 0.16 g/ml was selected as the cloud point at room temperature since its absorbance was very low and yet from the turbidity of solution, the sample solution of 0.16 g/ml concentration was at the edge of becoming cloudy.

5. This sample was utilized to develop a temperature vs. absorbance plot, and compared with the concentration vs. absorbance plot to get the relationship between temperature and concentration.

The cloud point temperature of the ternary system of polymer/solvent/water was also determined. Eudragit RL 100 was first dissolved in acetone under continuous stirring; then a certain amount of water was added and the solution was heated up to 50° C. for 30 minutes. After that the cuvette containing solution was slowly cooled in steps of 1° C. per minute. The cloud-point temperature was taken as the temperature at which the transmissivity of the solution decreased sharply and the solution changed from clear to turbid. A similar procedure was followed for PLGA in dioxane and water.

Transmissivity could also be used to determine the cloudiness of solution especially when the characteristic peak for polymer was not obvious or overlapping with the solvent if using an absorbance based determination. The higher the transmissivity % in the spectrophotometer reading for a wavelength range from 550 to 800 nm, the clearer the solution. In this case, the solution which had undergone precipitation will have relatively low % T (normally under 20%); so % T less than 20% was defined as cloudy, and % T greater than 80% was defined as clear.

Due to the limitation of resolution of a scanning electron microscope (SEM), a relatively large 550 nm diameter COSMO 55 (JGC Catalysts and Chemicals Ltd, Somerset, N.J.) nonporous spherical hydrophilic silica nanoparticles were utilized to act as the initial surrogate drug particles in the tests reported in this disclosure.

A scanning electron microscope (LEO 1530 Gemini, Zeiss, Thornwood, N.Y.) was employed for simple morphological observations. Dry coated particles were attached on the top of the pin stub mount. To examine the coating covering the nanoparticles, it was desired to coat this sample with carbon to make the sample conductive enough to get a clear surface structure picture since charging may occur when the specimen has poor electrical conductivity, causing distorted or deformed pictures.

A 200 kV Schottky field emission (JEOL JEM-2010F, Peabody, Mass.) analytical transmission electron microscope (TEM) was used for a more thorough analysis of the samples. Z contrast related high angle dark field images of the coated silica spheres were collected under Scanning transmission electron microscopy (STEM) mode to visualize the coating surrounding each individual sphere. The probe size of the electron beam was 1 nm so an accurate thickness could be determined from the STEM image directly. Energy-dispersive X-ray spectroscopy (Model 7246, Oxford Instruments, Concord, Mass.) provided the distribution of the elements on the surface of the nanoparticles.

A thermogravimetric analyzer (Pyris 1, PerkinElmer, Waltham, Mass.) was used to determine the amount of coating on the sample particles so that the coating thickness could be calculated by weight loss during heating. Laser diffraction spectroscopy (Vibri, Sympatec, Clausthal-Zellerfeld, Germany) was used to analyze particle size distribution and any agglomeration.

The results of cloud point studies for a number of binary and ternary systems were first considered. Then the various pre-treatments and post-treatments of the particle coating system were focused on. Finally, detailed characterization of the coated particles were provided.

Figure 4:
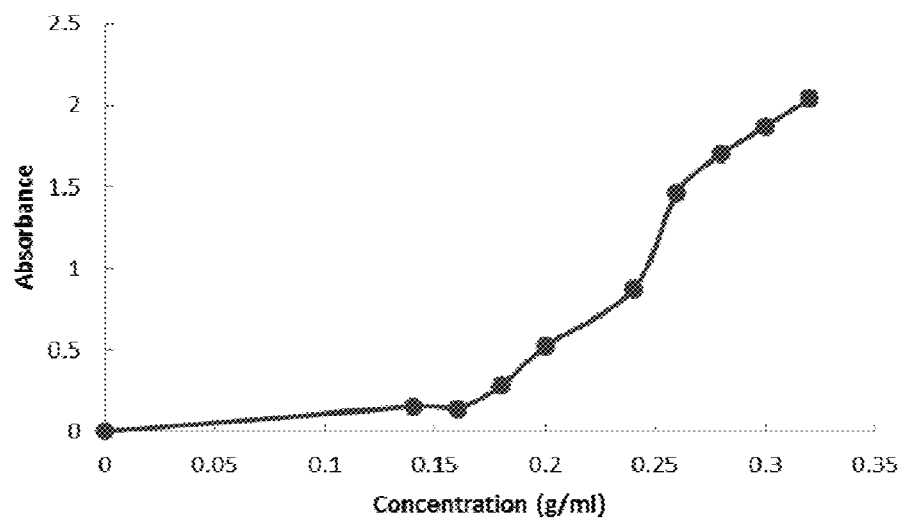
FIG. 4 is a graph that shows concentration vs. absorbance for Eudragit RL with acetone at 25° C.

The concentration vs. absorbance data for the acetone solution of Eudragit RL 100 at 25° C. are shown in FIG. 4.

The cloud point data for PLGA/dioxane (not shown) are similar to those for Eudragit RL 100/acetone in that the transmissivity of both solutions is around 100%; the solution remains clear with no precipitation-based particles appearing with a variation in temperature. That is because the cloud point temperature for both of these polymers dissolved in a pure solvent is very low; therefore it is difficult to have precipitation due to a temperature drop under mild conditions (e.g., 0° C. to 50° C.). It has been suggested (Hua et al., "*A facile preparation of highly interconnected macroporous poly(D,L-lactic acid-co-glycolic acid) (PLGA) scaffolds by liquid-liquid phase separation of a PLGA-dioxane-water ternary system,*" Polymer 44 (2003) 1911-1920) that when dissolving PLGA/Eudragit RL 100 into dioxane/acetone, addition of a little water decreases the solvation power of the solvent. The solution will turn from clear to cloudy depending on the temperature change. Therefore one can also adjust the cloud point of the system by adjusting the amount of water added.

A limited amount of antisolvent such as DI water was added to the solution containing Eudragit RL 100 to increase the cloud point temperature at the same polymer concentration. At the same cloud point temperature compared to the solution without addition of water, less polymer will be in solution if little DI water was added; further the solution viscosity will be lower making it easier to flow. A few different concentrations of water in the ternary system of polymer/solvent/water have been tested under different temperatures. The results are provided below for the two polymers studied.

Figure 5:
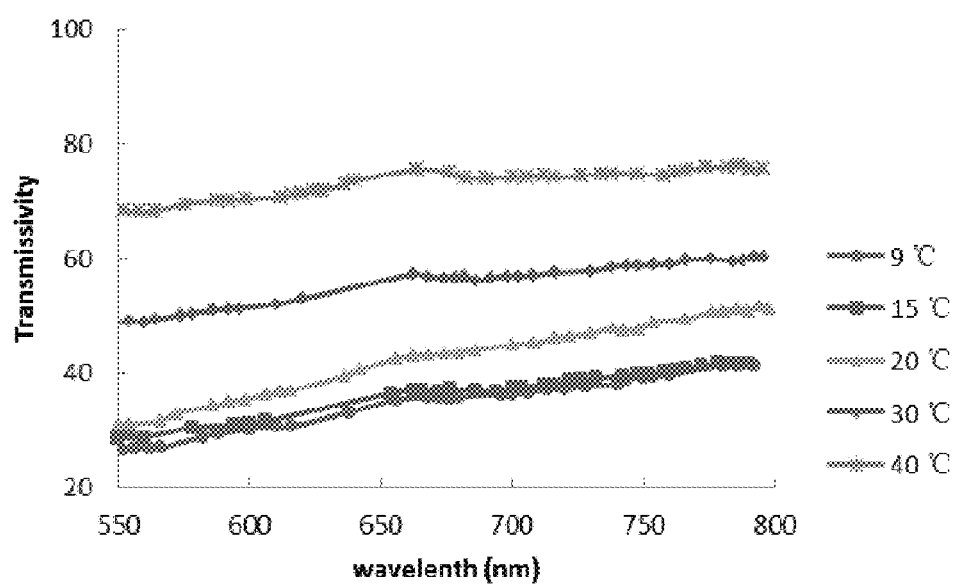
FIG. 5 is a graph that shows transmissivity of 10 wt % Eudragit RL100/2.5 ml acetone/0.5 ml water solution for different temperatures.

Different concentrations of Eudragit and the amount of water added in a Eudragit/acetone/water ternary system have been studied under different temperatures. FIG. 5 illustrates the behavior of one such solution; Table 2 provides a summary of the cloud point temperature observed for three different compositions of acetone/water. A ratio of 2.5/0.5 was selected to obtain the transmissivity vs. wavelength plot shown FIG. 5 since 15° C. is a modest temperature and was easy to achieve. Table 2 provides the actual cloud point temperatures for the Eudragit RL 100 solution.

TABLE 2

Cloud point temperatures vs. different ratios of acetone/water in Eudragit RL100 solution.

| Ratio of acetone/water (ml/ml) | Cloud point temperature of 10 wt % Eudragit RL100 (° C.) |
|---|---|
| 2.5/0.5 | 15 |
| 2.5/0.52 | 20 |
| 2.5/0.54 | 30 |

Different concentrations of PLGA and the amount of water added in the ternary system of PLGA/dioxane/water have also been tested under different temperatures. Compared to tests with Eudragit, the change from clear to cloudy status is easier to see through visual observations or transmissivity in UV.

Figure 6:
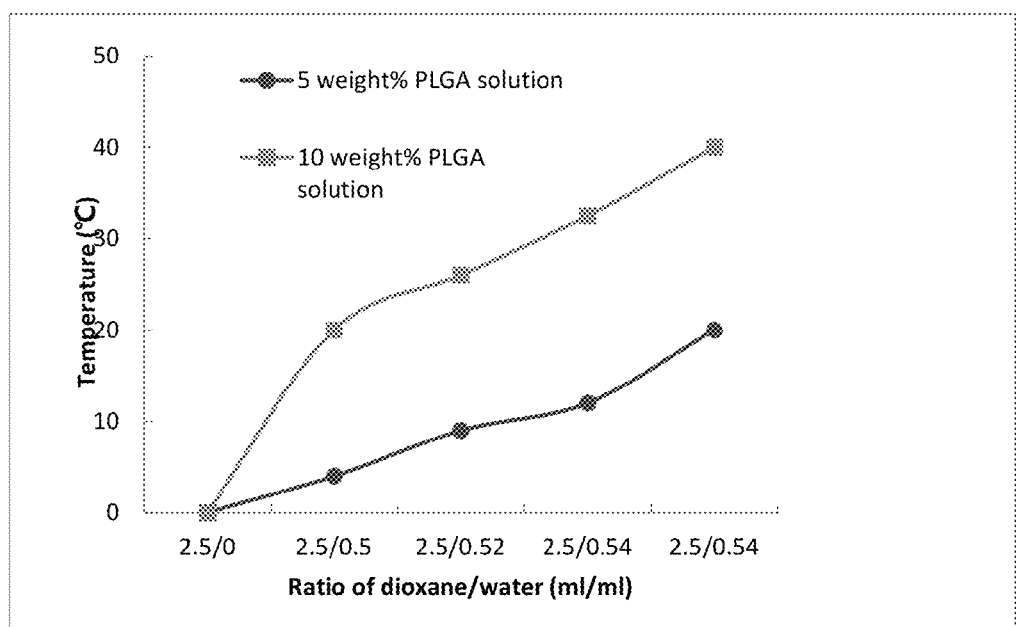
FIG. 6 is a graph that shows cloud point temperatures vs. different ratios of dioxane/water in PLGA solutions.

FIG. 6 provides a graphical summary of cloud point temperature vs. ratio of dioxane/water for PLGA. A ratio of 2.5/0.5 (dioxane/water) for 10 wt % PLGA solution or 2.5/0.56 for 5 wt % PLGA solution can be chosen for these tests since a temperature around 20° C. is a modest temperature and easy to achieve.

In certain embodiments, by adjusting the feed solution conditions, such as adding different amounts of water, different amounts of silica, adding a surfactant, and changing the residence time, the coating results were seen to be very different. As discussed above, the cloud point temperature of the two polymer solutions will change from clear to cloudy at higher (more easily realizable) temperatures when adding different amounts of water. Therefore for both polymer solutions, a small amount of non-solvent (water) was added.

Figure 7A:
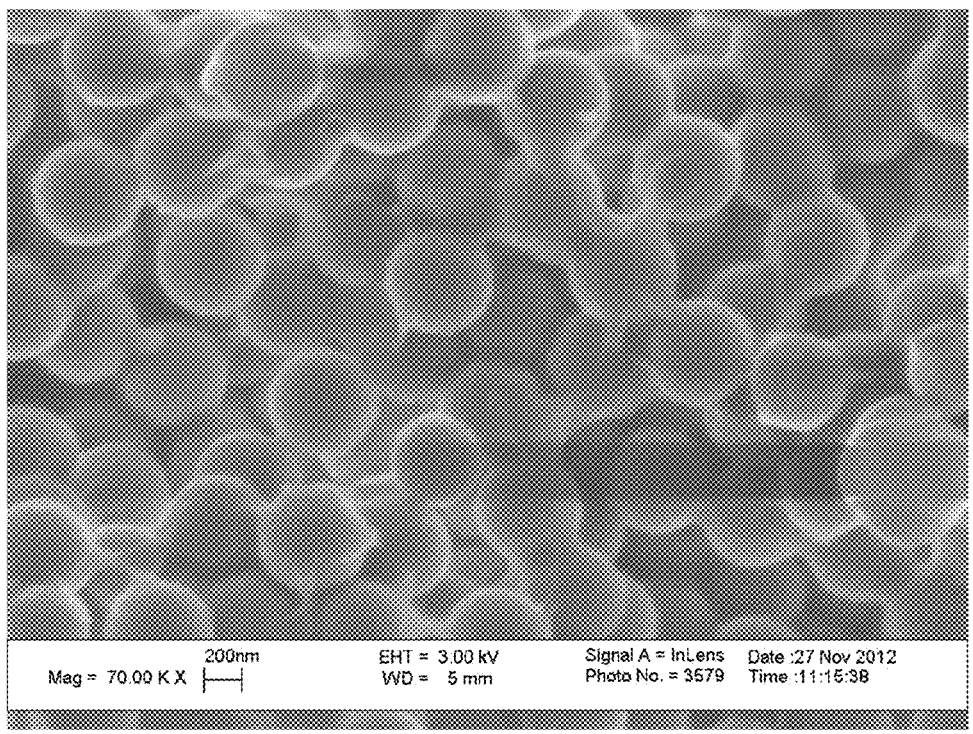
FIGS. 7A and 7B show: SEM photographs of coated particles in FIG. 7A without surfactant; and in FIG. 7B with surfactant (surfactant concentration 0.0035 M)
Figure 7B:
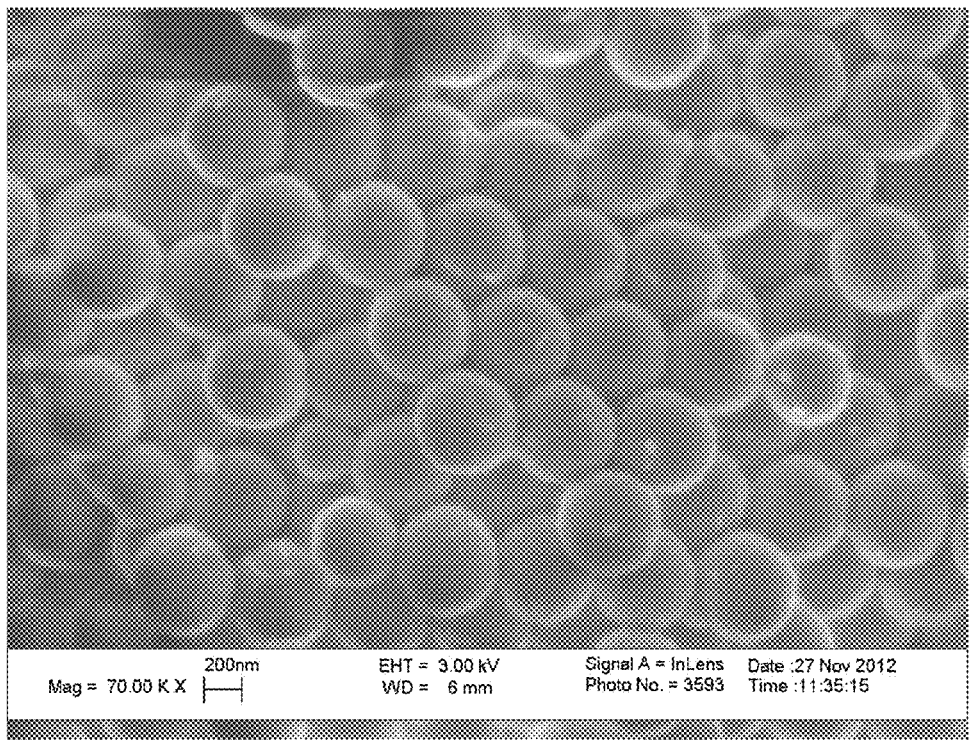

In further embodiments, particle agglomeration can be reduced by the addition of a surfactant, for example, sodium dodecyl sulfate, to the polymer solution. SEM photographs of coated particles with or without the addition of surfactant are shown in FIGS. 7A-B. With the addition of surfactant (FIG. 7B), the dispersion of the coated particles was much better as compared to those without the surfactant (FIG. 7A). The critical micelle concentration (CMC) of sodium dodecyl sulfate in pure water at 25° C. is 0.0082 M; therefore the concentration of SDS cannot be too high to prevent formation of micelles which can accelerate agglomeration.

Figure 8:
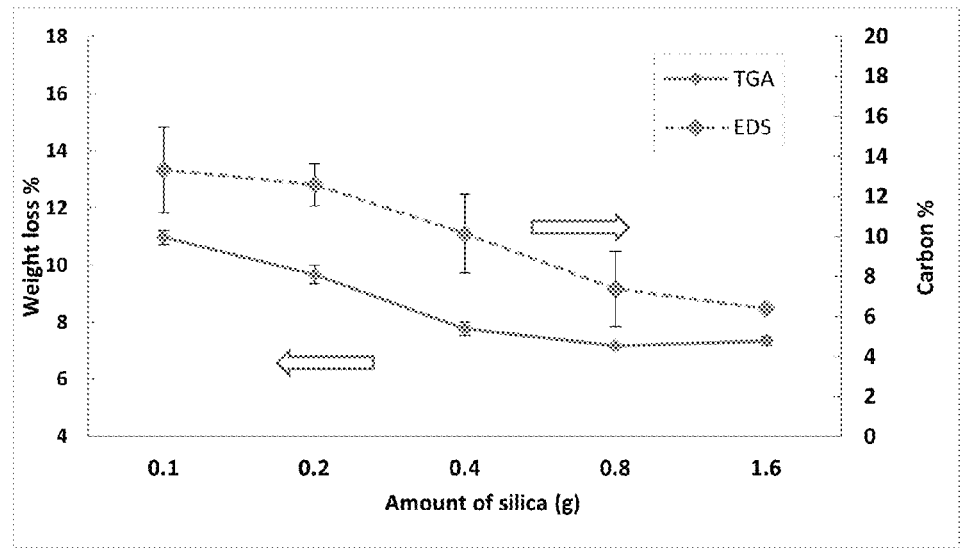
FIG. 8 is a graph that shows TGA and EDS results for different amounts of silica addition.

FIG. 8 shows the weight loss (percentage) of the coated particles obtained from TGA testing using different amounts of silica added to Eudragit RL 100 solution; FIG. 8 also shows EDS results based on the % carbon which was present on the coatings.

The TGA results indicate that with more silica added to the solution, the weight loss % is less which implies that the coating thickness around the particles is lower (more details on the TGA technique are provided below). When the amount of silica added exceeds a certain level (over 0.8 g), the coating thickness no longer decreases and remains relatively constant. Thus, both a too low or a too high silica concentration is undesirable; too low a concentration will make the coating thickness on individual particles larger, and too high a concentration will have little effect on the coating thickness, increase the pressure drop, and could result in the possibility of clogging the lumen of hollow fibers. As seen in FIG. 8, the EDS results reinforce those obtained from the TGA.

Figure 9:
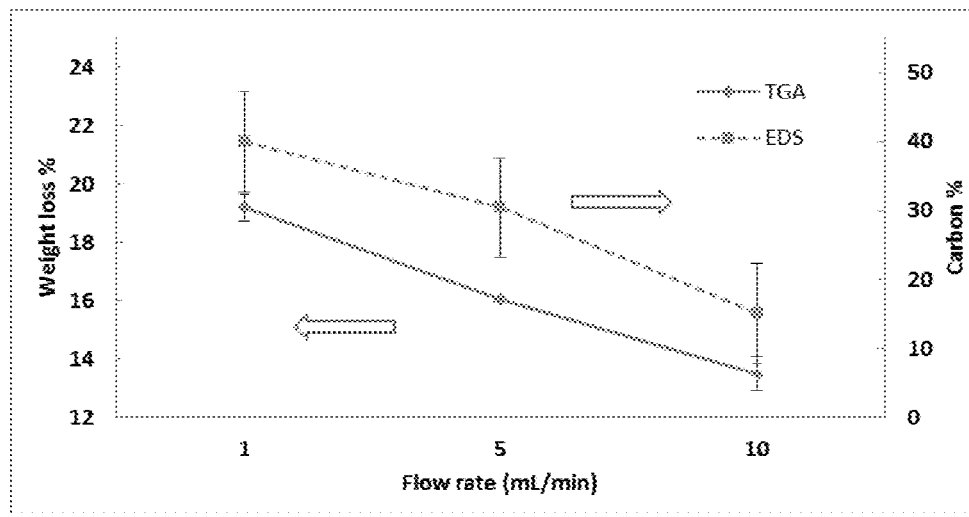
FIG. 9 is a graph that shows TGA and EDS results for coated nanoparticles for different residence times.

The residence time is also important for micron/nanoparticle coating; a longer residence time will lead to more polymer precipitating and a thicker coating. In certain embodiments, variation of residence time can be achieved by changing the feed flow rate into the SHFCC. FIG. 9 shows TGA and EDS results corresponding to flow rates of 1, 5, and 10 ml/min, respectively. The TGA results show that as the flow rate increases, the weight loss % decreases which indicates that the coating thickness decreases when the residence time decreases. EDS results support the same conclusion.

Figure 10A:
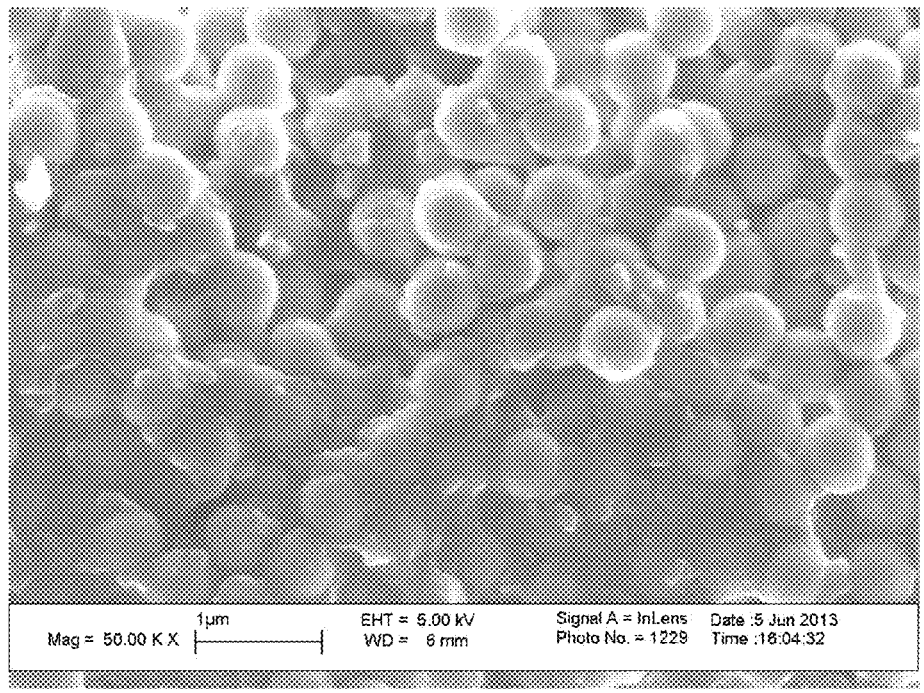
FIGS. 10A-C are SEM photographs of coated particles for different feed flow rates.
Figure 10B:
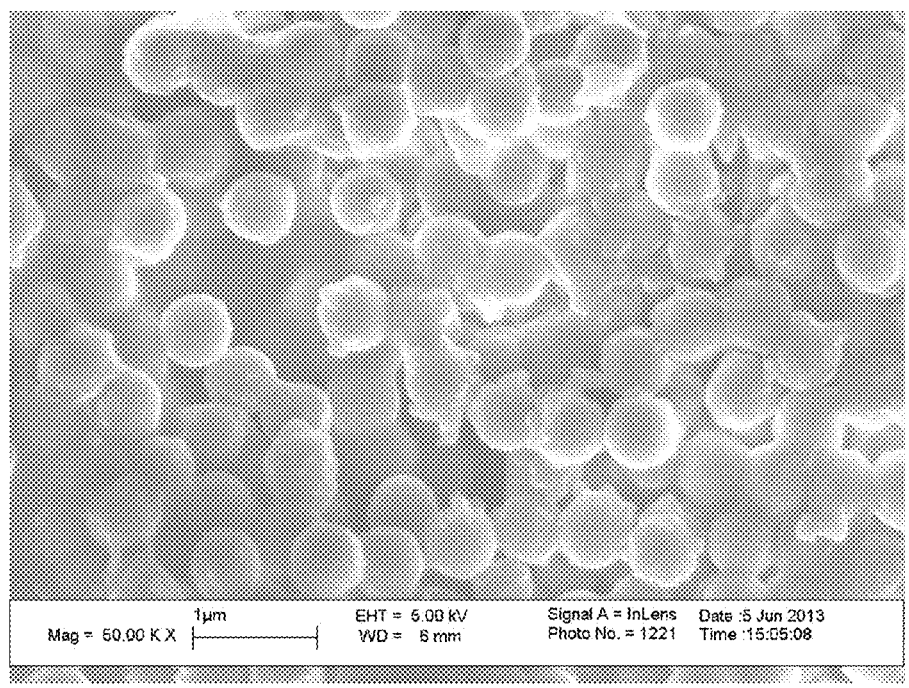
Figure 10C:
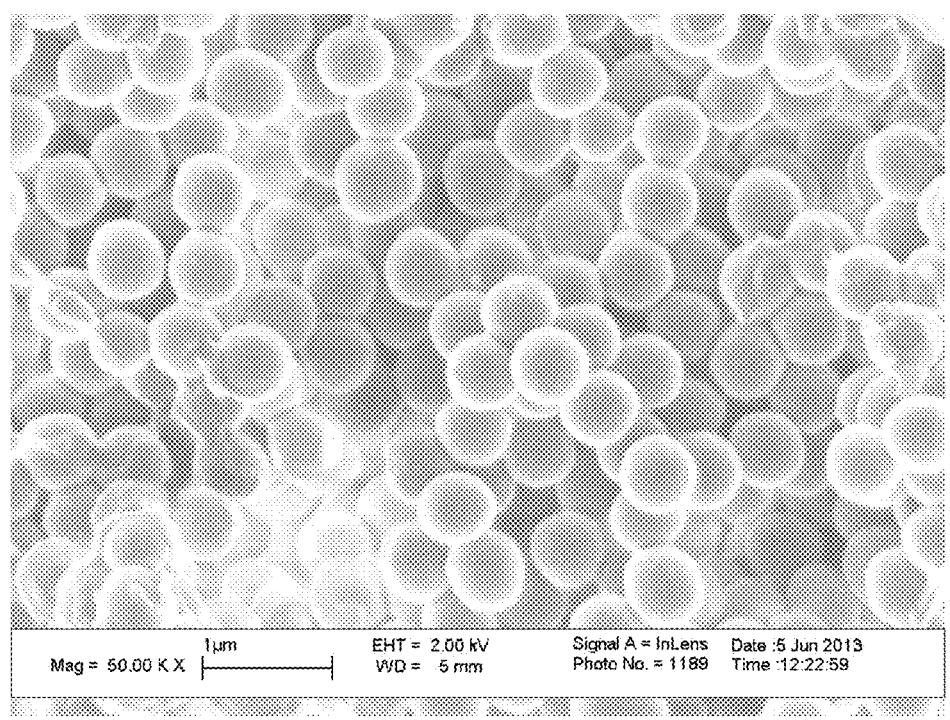

FIGS. 10A-C show SEM micrographs of coated particles for three of the flow rates shown in FIG. 9. Polymer coating on the nanoparticles is seen to be less thick when the flow rate is increased, (e.g., residence time is lowered); agglomeration between the particles also appears to decrease as the feed solution flow rate increases.

A number of post-treatment strategies were explored including improved vacuum filtration speed, addition of acetone, and sonication after filtration and centrifugation. They are considered one by one below.

Figure 11A:
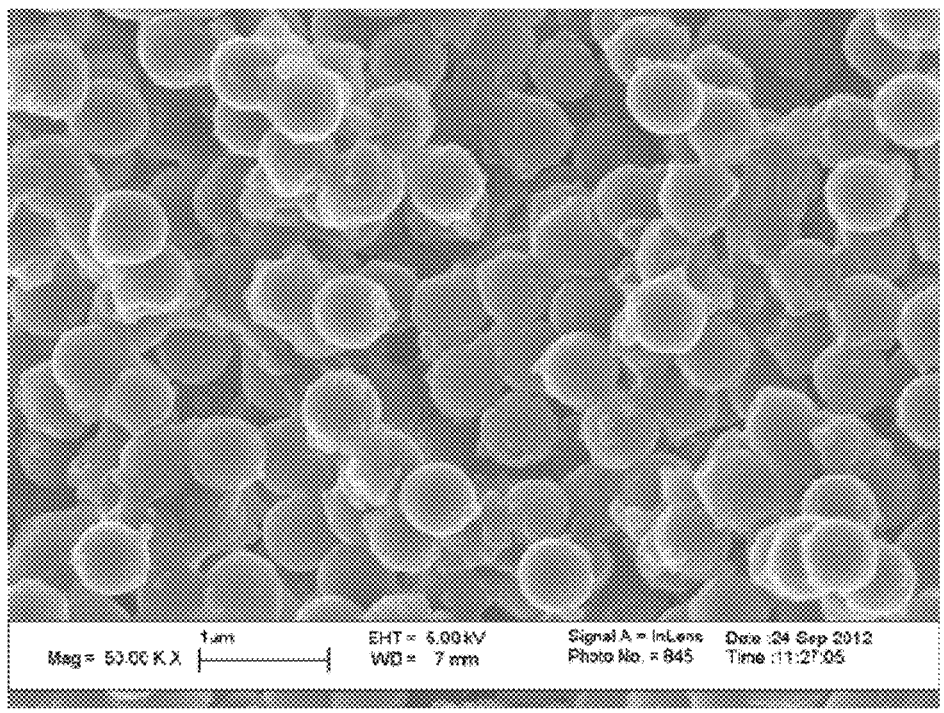
FIGS. 11A-B are SEM photographs of coated particles at different filtration rates.
Figure 11B:
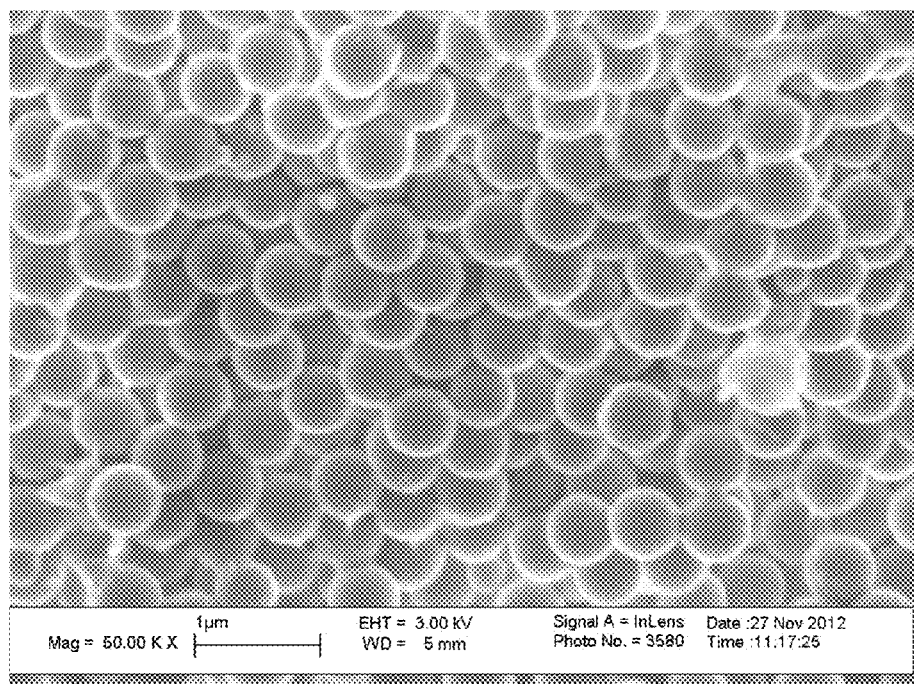

In certain embodiments, the thickness of the coating on the particles was reduced by incorporating a vacuum filtration device that can increase the filtration rate. Using this filtration device, the filtration rate was increased substantially by enhancing the vacuum level from 1 in Hg to 5 in HG and up to 16 in Hg, so that the excess polymer solution would not stay in contact with the particles to form additional coating. The results of the enhanced vacuum filtration for such embodiments are shown in FIGS. 11A-B and Table 3.

The SEM, TGA, and EDS studies all indicated that the faster the filtration rate, the thinner the coating. Particle agglomeration is also much less because the polymer solution remaining on the filter paper is extracted before it can form an additional coating on the surface of the particles or liquid bridges between the particles which will lead to agglomeration. Since the filtration rate was found to be important, the subsequent tests were run at the highest filtration rate (16 in Hg).

TABLE 3

TGA and EDS results for coated nanoparticles under slow and fast filtration conditions.

| Vacuum Level | 1 in Hg | 16 in Hg |
|---|---|---|
| TGA Weight loss % | 44.9 | 17.8 |
| EDS Carbon % | 37.0 | 31.2 |

Figure 12A:
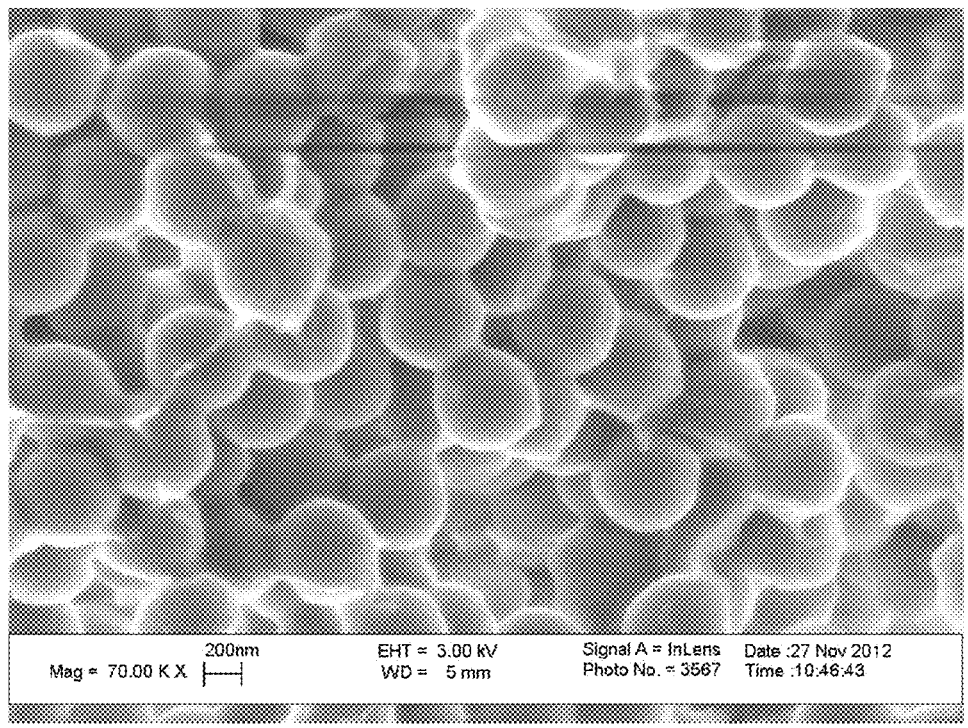
FIGS. 12A-C are SEM photographs of coated particles for different amounts of acetone introduced.
Figure 12B:
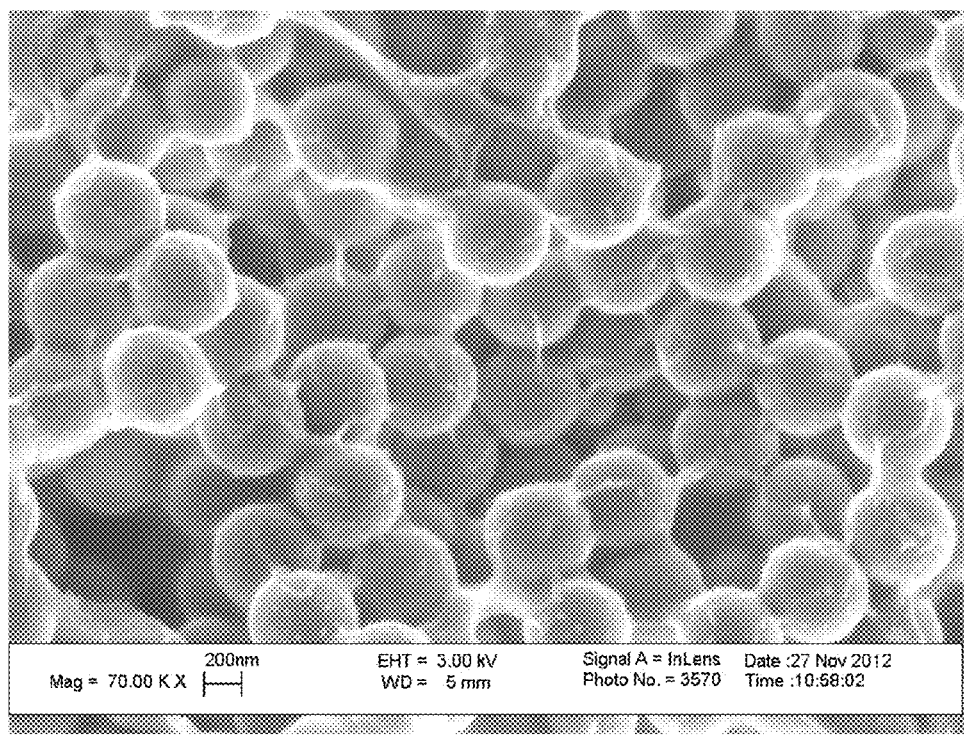
Figure 12C:
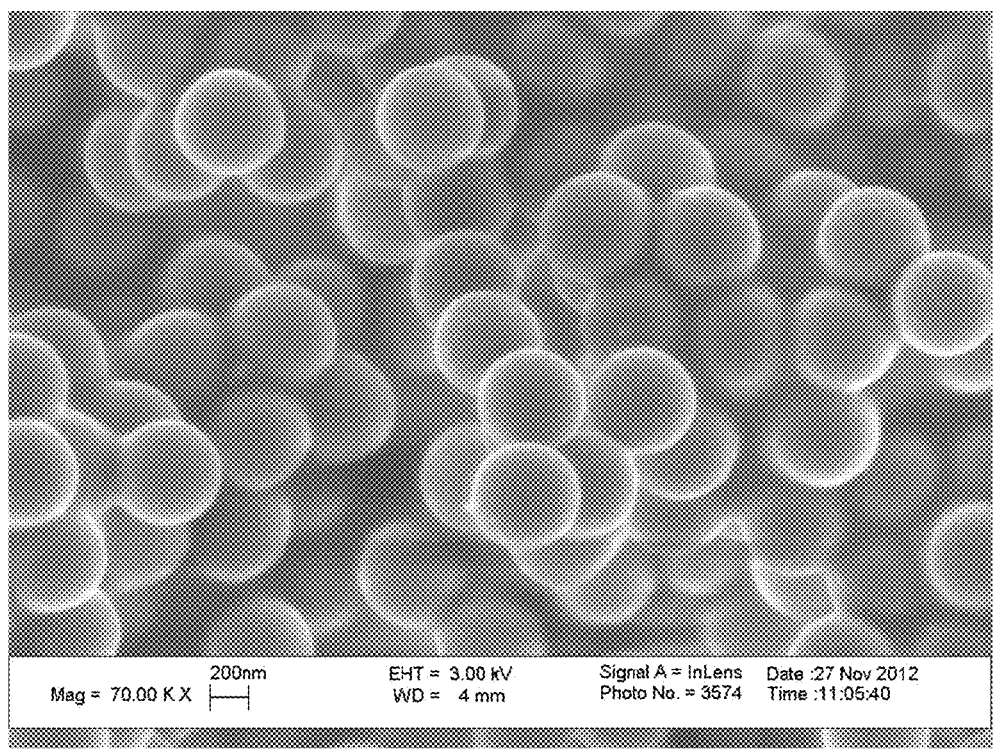

Another way to control the coating thickness in certain embodiments is by adding a small amount of acetone as part of the post-treatment. After collecting the samples on the filter paper, a few drops of acetone were dropped on the filter paper to remove excess coating. The residue was then collected and subjected to vacuum drying for characterization. Tests consisted of adding three different numbers of acetone drops; SEM images for three of these tests (3, 5 and 15 drops of acetone added) are shown in FIGS. 12A-C. The higher the number of drops of acetone added to the filter paper, the lesser the amount of coating observed on the particles; this means that the thickness of the coating may be controlled by using different amounts of acetone to post-treat the coated nanoparticles. However the method may be impractical in some cases as some of the coated particles were difficult to dislodge from the filter paper.

Above, the use of post-treatment sonication after both filtration and centrifugation as a means of producing free-flowing particles was discussed. Experimental results of Eudragit RL 100 coated particles obtained using sonication after fast filtration are shown in FIGS. 13A-B and compared to those without the sonication post-treatment. There is almost no excess polymer on the particles in FIGS. 13B1-2 compared with those in FIGS. 13A1-2, and agglomeration between particles is less than that in FIGS. 13A1-2. By using this post treatment method, the products were free-flowing rather than cohesive due to particles sticking together for these embodiments.

Sonication was also utilized as a post-treatment after centrifugation for further embodiments of the present disclosure. Similar to the results obtained by adding sonication after filtration, free flowing particles were also obtained by adding sonication as a post treatment after centrifugation.

Figure 14:
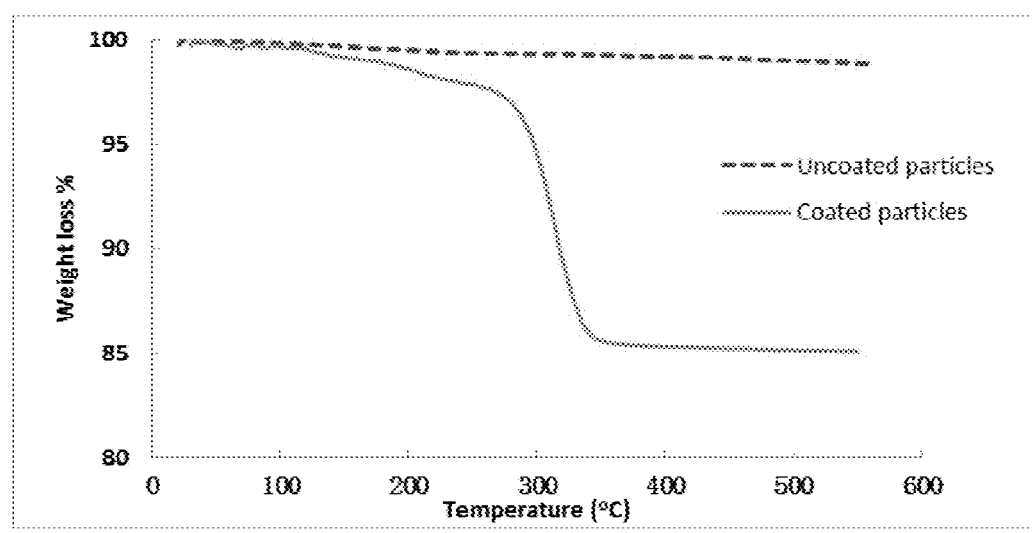
FIG. 14 is a TGA micrograph for Eudragit coated nanoparticles under post treatment method after filtration.

Thermogravimetric analysis (TGA) allows measurement of the change in particle mass as a function of time by increasing the temperature of the sample continuously. Samples of dry, coated particles and dry, uncoated Cosmo 55 silica particles were analyzed by TGA. The temperature in the TGA was increased at a rate of 10° C./min until it reached 550° C. During this period, Eudragit RL 100 polymer coating decomposed as a result of heating while the mass of the uncoated silica remained almost unchanged as seen in FIG. 14.

The solid line shows that the weight % of the coated particles was reduced from 100% to about 85%, which means that the 15% weight loss was due to decomposition of the polymer coated on the particles during heating.

To estimate the thickness of the coating (Wang et al., "Polymer Coating/encapsulation of Nanoparticles using a Supercritical Anti-solvent Process," J. Supercritical Fluids, 28, 84 (2004)), it was assumed that the polymer was evenly coated on the spherical nanoparticles of radius r and forms a uniform layer. The equation governing the relation between the mass of the polymer and the mass of the particles is:

$$\frac{m_{Silica}}{m_{Polymer}} = \frac{\rho_{Silica}\frac{4}{3}\pi r^3}{\rho_{Polymer}\frac{4}{3}\pi\{(r+h)^3 - r^3\}} \quad \text{(Equation 1)}$$

The coating thickness h can be calculated as:

$$h = r(1 + \rho_{Silica} m_{Polymer}/\rho_{Polymer} m_{Silica})^{1/3} - r \quad \text{(Equation 2)}$$

where $m_{Silica}$ and $m_{Polymer}$ are the mass of the particles and polymer, respectively. The densities of the host particles and polymer are $\rho_{Silica}$ (2.65 g/ml) and $\rho_{Polymer}$ (1.1 g/ml), respectively. Using the results from the TGA, the coating thickness for the nanoparticles under optimized conditions is about 20 nm.

Scale-up can be achieved by simply using a larger module containing, for example, double the number of hollow fibers, 46 instead of 23 (see Table 1). The 25 mm diameter filter paper used with the smaller module was replaced by a 90 mm diameter filter paper so as to be able to handle a larger amount of product. Since the number of fibers inside the SHFCC module was doubled, the flow rate was also doubled without affecting the residence time (e.g., the velocity in each hollow fiber remains the same). Therefore the larger module produced the same coated particles as the smaller module. Coated particles collected from both modules, large and small, were characterized by TGA. Further embodiments could be scaled up and up by continuing to use more and more hollow fibers until the desired size is achieved.

Figure 15:
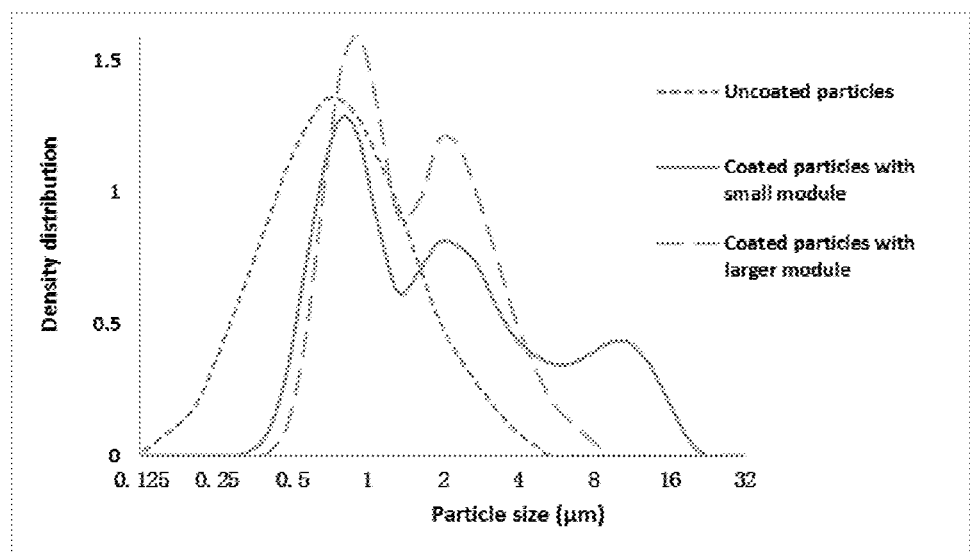
FIG. 15 is a graph showing particle size distribution for uncoated and Eudragit coated nanoparticles in both the small and large modules.

Sympatec Laser diffraction spectroscopy (LDS) coupled with RODOS dry dispersion and R1 lens (0.1-35 μm) was used to identify the particle size distribution (PSD) of the products collected. Importantly, it can identify the amount of agglomeration present in the coated particles. A dry powder of particles coated in the small module was tested under different pressures (0.5 bar to 3 bar) to determine the average particle size. With an increase of the pressure, the powder exhibited a reduction in particle size until a plateau was observed. After the pressure reached 3 bar, the particle size did not decrease as the pressure was increased which means that complete dispersal was achieved. Therefore the default primary pressure (PP) was set as 3 bar when measuring the PSD of the samples in FIG. 15.

The LDS analyzer was used to measure the PSD of uncoated Cosmo 55 silica, Eudragit coated particles in the small module, and Eudragit coated particles in embodiments utilizing the large module. Table 4 shows that the Sauter mean diameter ($D_s$) of the 3 samples are 640 nm, 1310 nm and 1250 nm, respectively. This indicates that the coated particles were somewhat agglomerated, forming mostly doublets and perhaps some triplets. After scale-up, the mean size of the coated particles from the large module was similar to those from the small module.

TABLE 4

Particle size for uncoated and coated nanoparticles.

| | $d_{10}$ (μm) | $d_{50}$ (μm) | $D_s$ (μm) |
|---|---|---|---|
| Uncoated particles | 0.33 | 0.77 | 0.64 |
| Coated particles with small module | 0.64 | 1.68 | 1.31 |
| Coated particles with large module | 0.71 | 1.44 | 1.25 |

Figure 16A:
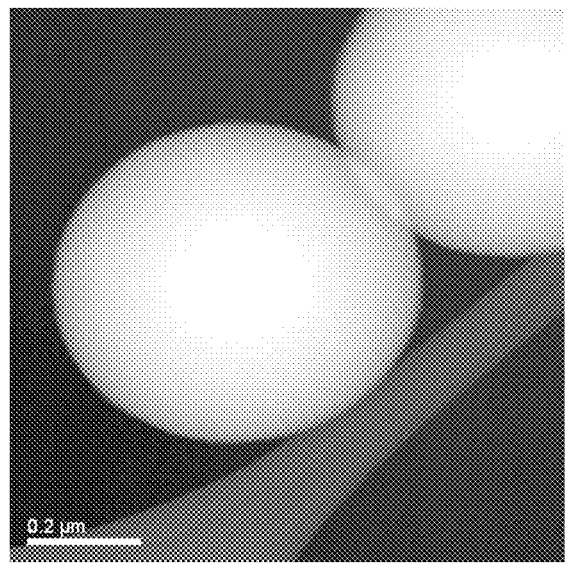
FIGS. 16A-B are STEM micrographs of uncoated nanoparticles (FIG. 16A) and coated particles under optimized condition (FIG. 16B)
Figure 16B:
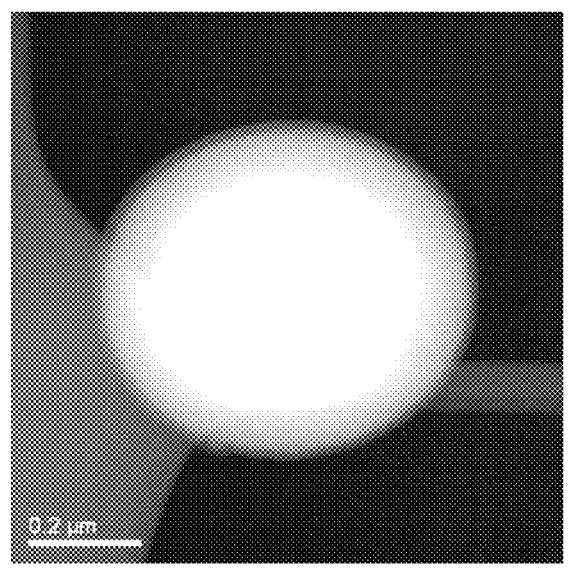

The particle coating thickness and morphology can be much more precisely determined by TEM-STEM analysis which is used to check whether the coating thickness is in accord with the TGA results and also if it is uniform. FIG. 16B shows a photograph of a single coated particle under optimized conditions (e.g., 0.4 g silica, 2.5 cc/min flow rate, surfactant concentration 0.0035 M, with 4 ml water, sonication post treatment after filtration at 16 in Hg filtration rate, small module). The bright area is the silica particle and the transparent grey ring represents the polymer coating. From FIG. 16B, it is easy to see that a uniform, thin coating is covering the particle, while for an uncoated silica particle shown in FIG. 16A no transparent ring is seen. Based on the scale bar, the thickness of the coating around the single nanoparticle can be estimated to be about 25 nm. This shows that embodiments of the present disclosure apply a uniform coating of which the thickness is variable depending on conditions.

Figure 17:
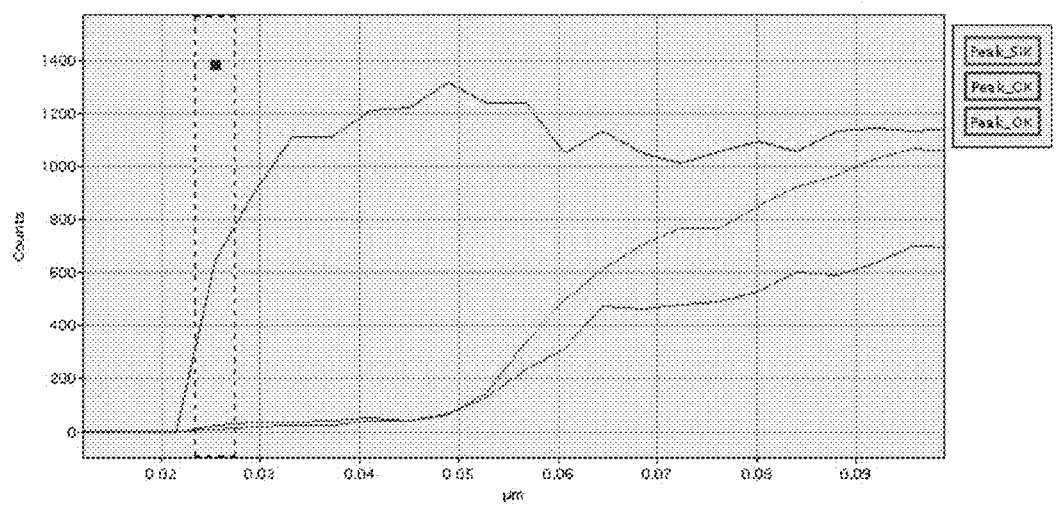
FIG. 17 is a graph showing EDS results of single coated nanoparticles under optimized conditions.

FIG. 17 shows the signal profile of various elements (carbon, silicon and oxygen) in the coated nanoparticle shown in FIG. 16B. The probe detects various elements in the particle from the surface to the interior. The point at 0.022 μm in the x-axis is the surface point of the coating; the point at 0.05 μm is the coating end point and the beginning of the surface of the silica particle. The coating thickness can then be estimated as 0.028 μm or 28 nm.

Figure 18A:
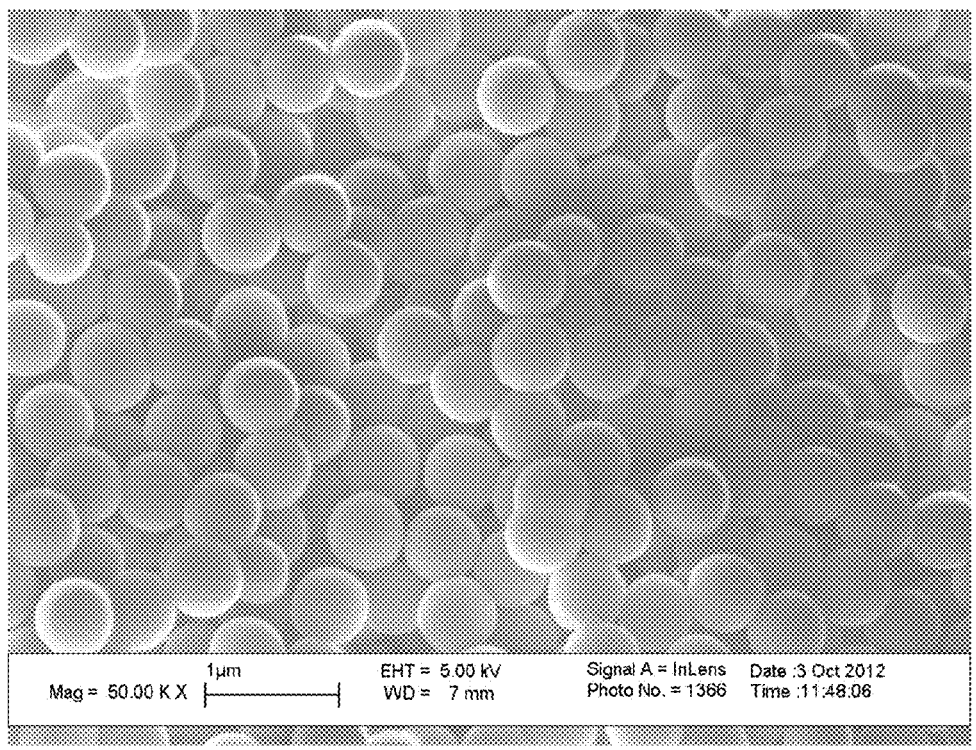
FIGS. 18A-B are SEM photographs of solutions with PLGA and nanoparticles before passing through the SHFCC (FIG. 18A), and after precipitation in the SHFCC (FIG. 18B).
Figure 18B:
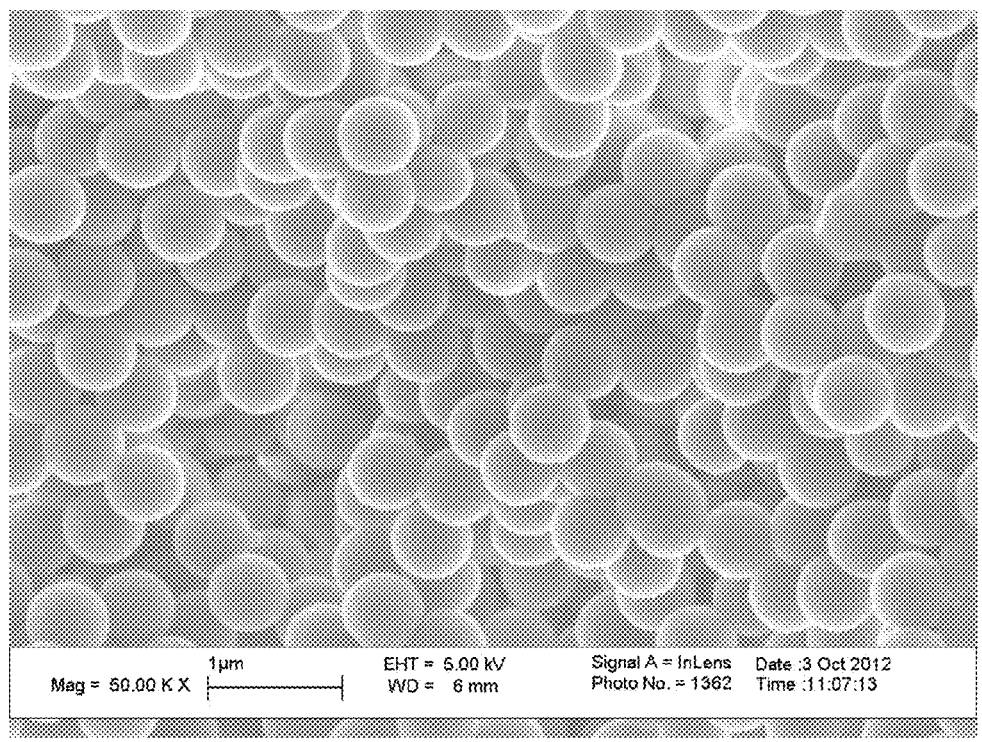

Coating the silica particles with PLGA was also studied in the SHFCC device (but not nearly as extensively as with Eudragit). FIG. 18B is shown here which indicates that PLGA can also be coated onto the silica particles in the SHFCC device. FIG. 18A shows an SEM image of silica particles in a dioxane solution of PLGA before precipitation, and FIG. 18B shows an SEM image of coated particles after the solution was passed through the SHFCC and precipitation occurred.

There is no coating in FIG. 18A; however FIG. 18B shows a uniform polymer coating covering the particles. This result is in accord with the EDS result that shows a carbon % of 21.6 after post-treatment using the fast filter (16 in Hg), confirming that PLGA can also be used to coat the particles by the SHFCC method.

In exemplary embodiments, a novel SHFCC crystallizer/heat exchanger was utilized to continuously coat nanoparticles with polymers from a polymer solution. The cloud point of the polymer solution was determined by UV spectrophotometry for the polymer-solvent-non-solvent systems of Eudragit RL100/acetone/water and PLGA/dioxane/water. The cloud point temperature of these systems was in the range of 15-25° C. Pre-treatment conditions employed included adding suitable amounts of a non-solvent (water) and surfactant (sodium dodecyl sulfate), varying the ratio of nanoparticle to polymer, and changing the flow rate (residence time) of the nanoparticle containing solution. Post-treatment methods for treating the coated particles such as very rapid filtration, centrifugation, and sonication were developed to control the thickness of the coating and the free-flowability (non-agglomeration) of the coated particles. This novel crystallization/coating method is attractive for polymer coating of nano-pharmaceuticals since scale-up is relatively simple and coated particles can be mass produced continuously.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

The invention claimed is:

1. A method for coating particles comprising:
   a) providing a polymer solution containing a suspension of particles;
   b) flowing the polymer solution through a lumen of a hollow fiber; and
   c) passing a cooling fluid around the exterior of the hollow fiber to cool the polymer solution and allow for polymer nucleation on the particles, with precipitated polymer forming a film around the particles to form uniformly coated and free-flowing coated particles.

2. The method of claim 1, wherein the particles in the polymer solution have a particle size of about 1 nm to about 10 microns.

3. The method of claim 1, wherein the hollow fiber is a polymeric hollow fiber, the polymeric hollow fiber having a solid non-porous and non-permeable wall that defines the lumen.

4. The method of claim 1, wherein the polymer solution includes a copolymer of ethyl acrylate, methyl methacrylate and a content of methacrylic acid ester.

5. The method of claim 1, wherein the polymer solution includes Poly(D,L-lactide-co-glycolide.

6. The method of claim 1, wherein the hollow fiber is fabricated from polypropylene.

7. The method of claim 1, wherein the hollow fiber has an internal diameter of about 420 μm and an outer diameter of about 575 μm.

8. The method of claim 1, wherein the polymer solution includes acetone, water and a surfactant.

9. The method of claim 1, wherein the polymer solution is pumped through the lumen of the hollow fiber at a rate of about 2.5 ml/minute.

10. The method of claim 1, wherein the cooling fluid includes ethylene glycol.

11. The method of claim 1, wherein the cooling fluid is configured to cool the polymer solution from about 55° C. to about 5° C. to form the coated particles.

12. The method of claim 1, further comprising the step of: d) filtering the solution containing the coated particles that exits the hollow fiber.

13. The method of claim 12, further comprising the step of: e) adding water under sonication to the filtered coated particles.

14. The method of claim 12, wherein step d) includes utilizing a vacuum filtration device.

15. The method of claim 1, further comprising the step of: d) centrifuging the solution containing the coated particles that exits the hollow fiber.

16. The method of claim 15, further comprising the step of: e) adding water under sonication to the centrifuged coated particles.

17. The method of claim 1, wherein the polymer solution includes sodium dodecyl sulfate.

18. The method of claim 1, wherein the coating thickness of the polymer film on the coated particles is about 20 nm.

19. A method for coating particles comprising:
   a) providing a polymer solution containing a suspension of particles, the particles in the polymer solution having a particle size of about 1 nm to about 10 microns;
   b) flowing the polymer solution through lumens of a plurality of polymeric hollow fibers; and
   c) passing a cooling fluid around the exterior of the plurality of the polymeric hollow fibers to cool the polymer solution and allow for polymer nucleation on the particles, with precipitated polymer forming a film around the particles to form uniformly coated and free-flowing coated particles.

20. A method for coating drug particles comprising:
   a) providing a polymer solution containing a suspension of drug particles, the drug particles in the polymer solution having a particle size of about 1 nm to about 10 microns;
   b) pumping the polymer solution through lumens of a plurality of polymeric hollow fibers, each polymeric hollow fiber having a solid non-porous and non-permeable wall that defines its respective lumen;
   c) passing a cooling fluid around the exterior of the plurality of the polymeric hollow fibers to cool the polymer solution and allow for polymer nucleation on the drug particles, with precipitated polymer forming a film around the drug particles to form uniformly coated and free-flowing coated drug particles;
   d) filtering the solution containing the coated drug particles that exits the hollow fibers; and
   e) adding water under sonication to the filtered coated drug particles.

* * * * *